US008263561B2

(12) United States Patent
Saeed

(10) Patent No.: US 8,263,561 B2
(45) Date of Patent: Sep. 11, 2012

(54) COMPOSITION AND METHOD FOR INHIBITING, PREVENTING, OR AMELIORATING COMPLICATIONS ASSOCIATED WITH INGESTION OF A MEDICINAL, CHEMICAL, OR BIOLOGICAL SUBSTANCE OR AGENT

(75) Inventor: Mohammed Saeed, Ann Arbor, MI (US)

(73) Assignee: Amana Pharmaceuticals Corp., Ann Arbor, MI (US)

( * ) Notice: Subject to any disclaimer, the term of this patent is extended or adjusted under 35 U.S.C. 154(b) by 865 days.

(21) Appl. No.: 11/922,450

(22) PCT Filed: Jun. 16, 2006

(86) PCT No.: PCT/US2006/023503

§ 371 (c)(1), (2), (4) Date: Apr. 15, 2009

(87) PCT Pub. No.: WO2006/138571

PCT Pub. Date: Dec. 28, 2006

(65) Prior Publication Data

US 2009/0220553 A1 Sep. 3, 2009

Related U.S. Application Data

(60) Provisional application No. 60/691,044, filed on Jun. 16, 2005.

(51) Int. Cl.

| | |
|---|---|
| ***A61K 38/10*** | (2006.01) |
| ***A61K 9/00*** | (2006.01) |
| ***A61K 39/02*** | (2006.01) |
| ***A61K 39/108*** | (2006.01) |
| ***C07K 7/00*** | (2006.01) |
| ***C07K 7/08*** | (2006.01) |
| ***C07K 4/00*** | (2006.01) |
| ***C07K 4/04*** | (2006.01) |

(52) U.S. Cl. ..... 514/21.4; 514/1.1; 530/326; 424/190.1; 424/236.1; 424/241.1

(58) Field of Classification Search ........................ None
See application file for complete search history.

(56) References Cited

U.S. PATENT DOCUMENTS 3,211,614 A 10/1965 Gunnar et al.
2004/0235879 A1 11/2004 Ware

FOREIGN PATENT DOCUMENTS

DK 2128447 12/1972
WO WO-2005/087797 9/2005

OTHER PUBLICATIONS

Rudinger J, "Characteristics of the amino acids as components of a peptide hormone sequence," Peptide Hormones, JA Parsons Edition, University Park Press, Jun. 1976, pp. 1-7.*

"Designing Custom Peptides," from SIGMA Genosys, pp. 1-2. Accessed Dec. 16, 2004.*

Schinzel R, Drueckes P, "The phosphate recognition site of *Escherichia coli* maltodextrin phosphorylase," FEBS, Jul. 1991, 286(1,2): 125-128.*

Berendsen HJC, "A Glimpse of the Holy Grail?" Science, 1998, 282: 642-643.*

Voet D, Voet JG, Biochemistry, Second Edition, John Wiley & Sons, Inc., 1995, pp. 235-241.*

Ngo JT, Marks J, Karplus M, "Computational Complexity, Protein Structure Prediction, and the Levinthal Paradox," The Protein Folding Problem and Tertiary Structure Prediction, K. Merc Jr. and S. Le Grand Edition, 1994, pp. 491-495.*

Bradley CM, Barrick D, "Limits of Cooperativity in a Structurally Modular Protein: Response of the Notch Ankyrin Domain to Analogous Alanine Substitutions in Each Repeat," J. Mol. Biol., 2002, 324: 373-386.*

Extended European Search Report for European Patent Application No. EP 11003537.5 mailed Sep. 5, 2011.

Chandran et al., Gastrointestinal disturbances in diabetes. Current Database Reports, vol. 3, No. 1 pp. 43-48, 2003.

* cited by examiner

*Primary Examiner* — Julie Ha

(74) *Attorney, Agent, or Firm* — Ropes & Gray LLP; Anita Varma; David P. Pleynet

(57) ABSTRACT

The present invention relates to a therapeutic composition comprising a pharmaceutically active agent and a diarrheagenic agent, wherein the diarrheagenic agent induces diarrhea to reduce the harmful or undesired side effects of the pharmaceutically active agent when the pharmaceutically active agent is ingested at a dose higher than the prescribed dose.

11 Claims, 6 Drawing Sheets

SEQUENCE LISTING

```
<160> NUMBER OF SEQ ID NOS: 11

<210> SEQ ID NO 1
<211> LENGTH: 18
<212> TYPE: PRT
<213> ORGANISM: Escherichia coli
```

-continued

<400> SEQUENCE: 1

Asn Thr Phe Tyr Cys Cys Glu Leu Cys Cys Asn Pro Ala Cys Ala Gly
1 5 10 15

Cys Tyr

<210> SEQ ID NO 2
<211> LENGTH: 19
<212> TYPE: PRT
<213> ORGANISM: Escherichia coli

<400> SEQUENCE: 2

Asn Ser Ser Asn Tyr Cys Cys Glu Leu Cys Cys Asn Pro Ala Cys Thr
1 5 10 15

Gly Cys Tyr

<210> SEQ ID NO 3
<211> LENGTH: 28
<212> TYPE: PRT
<213> ORGANISM: Vibrio cholerae

<400> SEQUENCE: 3

Phe Ile Lys Gln Val Asp Glu Asn Gly Asn Leu Ile Asp Cys Cys Glu
1 5 10 15

Ile Cys Cys Asn Pro Ala Cys Phe Gly Cys Leu Asn
20 25

<210> SEQ ID NO 4
<211> LENGTH: 17
<212> TYPE: PRT
<213> ORGANISM: Vibrio cholerae

<400> SEQUENCE: 4

Ile Asp Cys Cys Glu Ile Cys Cys Asn Pro Ala Cys Phe Gly Cys Leu
1 5 10 15

Asn

<210> SEQ ID NO 5
<211> LENGTH: 18
<212> TYPE: PRT
<213> ORGANISM: Vibrio cholerae

<400> SEQUENCE: 5

Leu Ile Asp Cys Cys Glu Ile Cys Cys Asn Pro Ala Cys Phe Gly Cys
1 5 10 15

Leu Asn

<210> SEQ ID NO 6
<211> LENGTH: 30
<212> TYPE: PRT
<213> ORGANISM: Yersinia enterocolitica

<400> SEQUENCE: 6

Gln Ala Cys Asp Pro Pro Ser Pro Pro Ala Glu Val Ser Ser Asp Trp
1 5 10 15

Asp Cys Cys Asp Val Cys Cys Asn Pro Ala Cys Ala Gly Cys
20 25 30

<210> SEQ ID NO 7
<211> LENGTH: 30
<212> TYPE: PRT
<213> ORGANISM: Yersinia enterocolitica -continued

```
<400> SEQUENCE: 7

Lys Ala Cys Asp Thr Gln Thr Pro Ser Pro Ser Glu Glu Asn Asp Asp
  1             5                   10                  15

Trp Cys Cys Glu Val Cys Cys Asn Pro Ala Cys Ala Gly Cys
             20                  25                  30


<210> SEQ ID NO 8
<211> LENGTH: 30
<212> TYPE: PRT
<213> ORGANISM: Yersinia enterocolitica

<400> SEQUENCE: 8

Ala Glu Cys Thr Gln Ser Ala Thr Thr Gln Gly Glu Asn Asp Trp Asp
  1             5                   10                  15

Trp Cys Cys Glu Leu Cys Cys Asn Pro Ala Cys Phe Gly Cys
             20                  25                  30


<210> SEQ ID NO 9
<211> LENGTH: 18
<212> TYPE: PRT
<213> ORGANISM: Escherichia coli

<400> SEQUENCE: 9

Asn Thr Phe Tyr Cys Cys Glu Leu Cys Cys Asn Pro Ala Cys Ala Gly
  1             5                   10                  15

Cys Tyr


<210> SEQ ID NO 10
<211> LENGTH: 19
<212> TYPE: PRT
<213> ORGANISM: Escherichia coli

<400> SEQUENCE: 10

Asn Ser Ser Asn Tyr Cys Cys Glu Leu Cys Cys Asn Pro Ala Cys Thr
  1             5                   10                  15

Gly Cys Tyr


<210> SEQ ID NO 11
<211> LENGTH: 18
<212> TYPE: PRT
<213> ORGANISM: Escherichia coli

<400> SEQUENCE: 11

Asn Thr Phe Tyr Cys Cys Glu Leu Cys Cys Asn Pro Ala Cys Ala Gly
  1             5                   10                  15

Cys Tyr
```

COMPOSITION AND METHOD FOR INHIBITING, PREVENTING, OR AMELIORATING COMPLICATIONS ASSOCIATED WITH INGESTION OF A MEDICINAL, CHEMICAL, OR BIOLOGICAL SUBSTANCE OR AGENT

RELATED APPLICATIONS

This application is a national stage filing under 35 U.S.C. §371 of International Application No. PCT/US2006/023503, filed on Jun. 16, 2006, which claims the benefit of the filing date of U.S. Provisional Application No. 60/691,044, filed on Jun. 16, 2005. The teachings of the referenced Applications are incorporated herein by reference in their entirety. International Application No. PCT/US2006/023503 was published under PCT Article 21(2) in English.

SEQUENCE LISTING

The instant application contains a Sequence Listing which has been submitted in ASCII format via EFS-Web and is hereby incorporated by reference in its entirety. Said ASCII copy, created on Jul. 29, 2011, is named 1033420001101 and is 3,788 bytes in size.

BACKGROUND

A therapeutic drug can be toxic or lethal if ingested at or above a specified dosage. A chemical substance or biological agent not intended for oral consumption can have dire health or safety consequences if ingested. Worldwide, thousands of accidental or intentional overdosing or poisoning incidents result in significant morbidity and mortality each year. Healthcare and other costs stemming from treating patients who suffer from complications associated with overdosing on medicines or ingestion of harmful chemical or biological substances or agents are staggeringly high.

A medication, a chemical substance, or a biological agent can be ingested beyond a safe quantity in any of a variety of contexts. For example, and without limitation, a child may ingest a sufficiently large quantity of a medicinal or other chemical or biological substance by mistaking the substance for candy or other food or drink; an adolescent or adult may ingest a harmful, or in some instances lethal, dose of an over-the-counter (OTC) or prescription medication in an attempt to commit suicide; a patient may inadvertently ingest an inappropriately high dose of a medication by misunderstanding a physician's, a pharmacist's, or a pharmaceutical manufacturer's instructions, or by mistaking one medication (and hence its permitted dosage) for another; and a patient being treated for drug addiction may overdose on, for example and without limitation, methadone, a synthetic opiate used to treat heroine dependence.

Methods to date have suggested applying to medicinal compositions an emetic coating to induce emesis (vomiting) and expel a toxic substance from the stomach. However, it has proven difficult to find an effective emetic preparation that has tolerable side effects in a broad patient population. Additionally, emesis carries the risk that a patient may gag during uncontrollable vomiting, and depending on his or her state of intoxication-suffer an accelerated death by asphyxiation Moreover, emesis is unsuitable for preventing potentially toxic or other harmful effects in certain contexts. This is at least in part because emesis essentially fails to expel a substance poised for absorption by the small or large intestine after the substance has already passed through the stomach.

Accordingly there is a need for an improved composition and method to inhibit, prevent, or ameliorate complications associated with ingestion, or typically an excessive ingestion, of a medicinal, chemical, and/or biological substance or agent. There is also a need for a composition and method to discourage intentional overdose on a medicinal, chemical, and/or biological substance or agent, for example and without limitation, a therapeutic composition such as a psychoactive drug.

SUMMARY OF THE APPLICATION

Accordingly, the present application provides methods and compositions to address such needs.

In one aspect, when a pharmaceutically active agent, which is safe when ingested at a recommended level or below a threshold amount, is ingested by a subject in excess, either by intentional or accidental overdose, and thereby becoming potentially lethal, toxic, or otherwise harmful or undesirable, the compositions and methods described herein reduce the likelihood of, or in some instances prevent, death, injury, or other harm by producing diarrhea in the subject ingesting the excess composition comprising the pharmaceutically active agent. The subject can be a human or an animal, preferably a mammal. In certain embodiments, the diarrhea is rapid and is induced by employing one or more biological, chemical, or biochemical compounds or agents having diarrheagenic properties. In certain embodiments, the diarrteagenic compounds have predictable and thus regulatable effects in a subject.

In certain embodiments, the application provides a therapeutic composition comprising a pharmaceutically active agent and a diarrhoetic or diarrheagenic agent. The diarrheagenic agent is a substance or agent capable of inducing diarrhea, if the therapeutic composition is taken at an undesirable high dose, for example, a dose exceeding a prescribed or otherwise safe or threshold quantity. If a subject takes a prescribed dose or a dose below a threshold amount, however, the pharmaceutical agent in the therapeutic composition has its proper or intended pharmacological effect, and the therapeutic composition would not induce diarrhea or other undesired side effects in the subject.

In certain embodiments, the diarrheagenic agent is coated onto the pharmaceutically active agent.

In certain embodiments, when the therapeutic composition is ingested by a subject at an appropriate level (e.g., prescribed dosage or below a threshold level), the cumulative amount of the diarrheagenic agent present in the subject is below a threshold level that is required to induce diarrhea. Accordingly, the pharmaceutically active agent is formulated in the therapeutic composition such that the agent will be released in the subject at a desirable level or dosage. When the therapeutic composition is ingested by a subject at a level exceeding an appropriate level (e.g., prescribed dosage or below a threshold level), the cumulative amount of the diarrheagenic agent present in the subject is above the threshold level that is required to induce diarrhea and thereby induces diarrhea. In certain embodiments, the diarrhea is rapid, or in certain instances, instant. Accordingly, the pharmaceutically active agent is formulated in the therapeutic composition such that the cumulative amount of the agent released in the subject will be lower than the amount of the agent that would have been released in the absence of the diarrhea.

In certain embodiments, the diarrheagenic agent is a toxin, a viral protein, a laxative, a ligand for an enterotoxin receptor, any analog of any of the foregoing, or any agent that is capable of inducing diarrhea in a subject, or any combination of the foregoing. Examples of toxins include, such as for example, a bacterial enterotoxin or an analog thereof, e.g., an STa peptide or its analog. An enterotoxin analog can be a peptidomimetic based on a naturally-occurring enterotoxin or a variant thereof. A naturally-occurring enterotoxin can be a peptide having an amino acid sequence of any of SEQ ID NOs: 1-10. An enterotoxin peptide can be a peptide having an amino acid sequence at least 70%, 75%, 80%, 85%, 90%, 95%, or 100% identical to any of SEQ ID NOs: 1-10. Accordingly, an enterotoxin peptide can be a naturally-occurring enterotoxin or a variant or mutant thereof. A mutant enterotoxin peptide may have amino acid mutations at 1, 2, 3, 4, 5, 6, 7, 8, 9, or 10 positions of any of SEQ ID NOs: 1-10. An amino acid mutation can be a substitution, a deletion, or an addition of the amino acid at the corresponding position of the respective amino acid sequence.

Examples of laxatives include, without limitation, aloe vera, bisacodyl, casanthranol, cascara sagrada, castor oil, dehydrocholic acid, phenolphthalein, picosulfate, senna, sennosides, or any combination thereof.

In certain embodiments, the diarrheagenic agent includes a ligand that binds an enterotoxin receptor, such as for example, the human guanylate cyclase-coupled heat stable enterotoxin receptor as described in de Sauvage et al., J. Biol. Chem. (1991) 266: 17912-17918. The ligand can be a small molecule (including a natural product, a synthetic molecule, or a metabolite) a peptide or a peptide analog (e.g., a peptidomimetic), a nucleic acid, an aptamer, a naturally-occurring ligand for the respective receptor, or a synthetic ligand (including mutant or variant of a naturally-occurring peptide ligand).

In certain embodiments, the diarrheagenic agent includes a peptide comprising guanylin, uroguanylin, or a combination thereof.

The pharmaceutically active agent of a therapeutic composition of the application can be any drug, biologic, or dietary supplement, or any combination thereof. In specific embodiments, the pharmaceutically active agent is a compound the overdose (e.g., ingestion by a subject at an inappropriate level or a level exceeding the recommended dosage) of which is harmful (e.g., toxic, injurious, or deadly) to a subject. The subject can be a human or animal patient in a general population or in a particular population. For example, a subject can be a pediatric patient, a pregnant or nursing woman, an elderly patient, or a patient having another condition or disease (e.g., an addiction to the pharmaceutically active agent or a hepatic disease) that makes the patient more vulnerable to a higher-than-desirable level of the specific pharmaceutically active agent or any pharmaceutically active agent.

In certain embodiments, the therapeutic composition comprises, a second coating (e.g., an enteric coating) that substantially envelops the first coating, and thereby reduces or inhibits the absorption of the therapeutic composition and/or the drug, chemical substance and/or biological agent of the therapeutic composition by the stomach.

Additionally, the enteric coating may inhibits, discourages, or prevents the diarrhoetic agent from being inactivated by the acidity of the environment of the stomach. When the composition reaches the small or large intestine, the diarrhoetic coating is available to interact with the small or large intestine essentially prior to absorption of the drug, chemical substance and/or biological agent of the composition. If a sufficient quantity of the composition (e.g., in the form of one or more medicinal pills) is ingested, severe and typically involuntary diarrhea ensues, expelling potentially harmful contents of the pills from the gastrointestinal (GI) tract.

Examples of enteric coatings include, without limitation, a hydrophilic polymer, an enteric polymer, a pH modifier, or any combination thereof.

In certain embodiments, a therapeutic composition of the present application comprises an agent that would deter tempering or breaking of the pharmaceutical composition to cause release of one or more pharmaceutically active agents included therein. Such an agent can be an irritant, such as for example, an irritant added to prevent someone from crushing a pill of an extended-release formulation and thereby destroying its extended-release characteristics as described in U.S. Patent Application Publication No. 20030125347.

Accordingly, certain embodiments of the application provides a therapeutic composition containing a medicinal, chemical, and/or biological substance or agent coated with a diarrhoetic compound; and a second protective coating to delay, reduce, discourage, or in some instances prevent, absorption of the therapeutic compound or the diarrhoetic coating in the stomach such that an overdose of the compound does not become lethal or otherwise unacceptably harmful.

In one embodiment, if the composition according to the application is ingested at an inappropriately high level (e.g., above a threshold level), the diarrhea-inducing compound acts in the small or large intestine to induce diarrhea, thereby expelling the therapeutic composition from the GI tract prior to the therapeutic composition being absorbed into the blood stream and producing toxic or other harmful effects.

Another aspect of the present application provides a diarrheagenic composition useful as a pharmaceutical coating, excipient, or carrier. The diarrheagenic composition comprises a diarrheagenic agent, such as for example, a laxative, a toxin (e.g., a bacterial enterotoxin such as STa) or a ligand for an enterotoxin receptor (e.g., a human guanylate cyclase-coupled receptor). The diarrheagenic composition can be combined with a pharmaceutical composition including one or more pharmaceutically or therapeutically active agents, and the composition is useful in preventing harmful effects, for example, those caused by accidental or intentional overdose of the pharmaceutical composition. In certain embodiments, the diarrheagenic composition may further comprise an agent that would deter tempering or breaking of the pharmaceutical composition to cause release of one or more pharmaceutically active agents included therein. Such an agent can be an irritant, such as for example, an irritant added to prevent someone from crushing a pill of an extended-release formulation and thereby destroying its extended-release characteristics as described in U.S. Patent Application Publication No. 20030125347. In certain embodiments, the diarrheagenic composition further comprises an enteric coating.

Accordingly, the application provides a composition for preventing or reducing potential harm from overdose ingestion, comprising: an amount of a core ingredient below a threshold dose; and a diarrheagenic coating enclosing the core ingredient and containing an amount of a diarrheagenic substance, the amount of the diarrheagenic substance being sufficient to cause diarrhea to expel at least a portion of the core ingredient from the gastro-intestinal tract of a specimen if the specimen ingests the composition approximately at or above the threshold dose, thereby reducing potential harm from overdose ingestion of the composition. The composition may further include a controlled-release coating containing a controlled-release substance to adjust at least one of a time and a venue of absorption of the core ingredient in the gastro-intestinal tract, the controlled-release coating interposed between, and separating, the core ingredient and the diarrheagenic coating. The composition may further include an enteric coating containing an enteric substance, the enteric coating enclosing the diarrheagenic coating to at least partially reduce premature absorption of at least one of the core ingredient and the diarrheagenic substance in the gastro-intestinal tract.

The application also provides a composition for preventing or reducing potential harm from overdose ingestion, comprising a mixture of: an amount of a core ingredient below a harmful threshold dose; and an amount of a diarrheagenic substance, the amount of the diarrheagenic substance being sufficient to cause diarrhea to expel at least a portion of the core ingredient from the gastrointestinal tract of a specimen if the specimen ingests the composition approximately at or above the threshold dose, thereby reducing potential harm from overdose ingestion of the composition. The composition may further include an enteric coating containing an enteric substance, the enteric coating enclosing the mixture of the core ingredient and the diarrheagenic substance to at least partially reduce premature absorption of at least one of the core ingredient and the diarrheagenic substance in the gastro-intestinal tract.

The application also provides a multiparticulate composition for preventing or reducing potential harm from overdose ingestion, comprising: a population of particulates containing a core ingredient, the aggregate amount of the core ingredient in the population adjusted below a threshold dose; and a diarrheagenic coating enclosing the population of the core ingredient particulates and containing an amount of a diarrheagenic substance, the amount of the diarrheagenic substance being sufficient to cause diarrhea to expel at least a portion of the core ingredient from the gastro-intestinal tract of a specimen if the specimen ingests the composition approximately at or above the threshold dose, thereby reducing potential harm from overdose ingestion of the composition. The multiparticulate composition may further include a controlled-release coating containing a controlled-release substance to adjust at least one of a time and a venue of absorption of the core ingredient in the gastrointestinal tract, the controlled-release coating interposed between, and separating, the population of the core ingredient particulates and the diarrheagenic coating. The multiparticulate composition may further include an enteric coating containing an enteric substance, the enteric coating enclosing the diarrheagenic coating to at least partially reduce premature absorption of at least one of the core ingredient and the diarrheagenic substance in the gastro-intestinal tract.

The application also provides a multiparticulate composition for preventing or reducing potential harm from overdose ingestion, comprising a population of particulates, at least one of the particulates containing: an amount of a core ingredient, the amount of the core ingredient being sufficiently low such that an aggregate amount of the core ingredient in the particulate population is below a threshold dose; and a diarrheagenic coating enclosing the core ingredient and containing an amount of a diarrheagenic substance, the amount of the diarrheagenic substance being sufficient to cause diarrhea to expel at least a portion of the core ingredient from the gastrointestinal tract of a specimen if the specimen ingests the composition approximately at or above the threshold dose, thereby reducing potential harm from overdose ingestion of the composition. The multiparticulate composition may further include a controlled-release coating containing a controlled-release substance to adjust at least one of a time and a venue of absorption of the core ingredient in the gastrointestinal tract, the controlled-release coating interposed between, and separating, the core ingredient and the diarrheagenic coating. In certain embodiments, the venue of absorption includes at least a portion of the small or large intestine. The multiparticulate composition may also include an enteric coating containing an enteric substance, the enteric coating enclosing the particulate population to at least partially reduce premature absorption of at least one of the core ingredient and the diarrheagenic substance in the gastro-intestinal tract. In certain embodiments, the enteric coating at least partially reduces the absorption of at least one of the core ingredient and the diarrheagenic substance in the stomach of the specimen.

The application further provides a multiparticulate composition for preventing or reducing potential harm from overdose ingestion, comprising a population of particulates, at least one of the particulates containing a mixture of: an amount of a core ingredient, the amount of the core ingredient adjusted so that an aggregate amount of the core ingredient in the particulate population is below a threshold dose; and an amount of a diarrheagenic substance, the amount of the diarrheagenic substance adjusted to cause diarrhea to expel at least a portion of the core ingredient from the gastrointestinal tract of a specimen if the specimen ingests the composition approximately at or above the threshold dose, thereby reducing potential harm from overdose ingestion of the composition. The composition may further include an enteric coating containing an enteric substance, the enteric coating enclosing the particulate population to at least partially reduce premature absorption of at least one of the core ingredient and the diarrheagenic substance in the gastro-intestinal tract.

In various aspects of application, the compositions may include an orally-administrable dosage form. In certain embodiments, the dosage form can be a tablet, a capsule, a sprinkle, a caplet, a granule, a spheroid, an ellipsoid, a bead, a pellet, a chewing gum, a lozenge, a crystal, or any combination thereof.

The core ingredient described herein may include a pharmacological ingredient, such as for example, a pharmaceutically active substance. Examples of the pharmaceutical ingredient include, without limitation, antidiabetic, analgesic, antiinflammatory agent, antirheumatic, anttihypotensive agent, anti hypertensive agent, psychoactive drug, tranquillizer, antiemetic, muscle relaxant, glucocorticoid, agent for treating an inflammatory bowel disease, antiallergic, antibiotic, antiepileptic, anticoagulant, antimycotic, antitussive, arteriosclerosis remedy, diuretic, protein, peptide, enzyme, enzyme inhibitor, gout remedy, hormone, hormone inhibitor, cardiac glycoside, immunotherapeutic agent, cytokine, laxative, lipid-lowering agent, migraine remedy, mineral product, otological agent, anti-Parkinson agent, thyroid therapeutic agent, spasmolytic, platelet aggregation inhibitor, vitamin, cytostatic inhibitor, metastasis inhibitor, phytopharmaceutical, chemotherapeutic agent, dietary supplement, and amino acid.

Further features and advantages of the application will be apparent from the following description of illustrative embodiments and from the claims.

BRIEF DESCRIPTION OF THE DRAWINGS

The following figures depict certain illustrative embodiments of the application in which like reference numerals refer to like elements. These depicted embodiments are to be understood as illustrative of the application and not as limiting in any way.

DETAILED DESCRIPTION OF ILLUSTRATIVE EMBODIMENTS

Figure 1A:
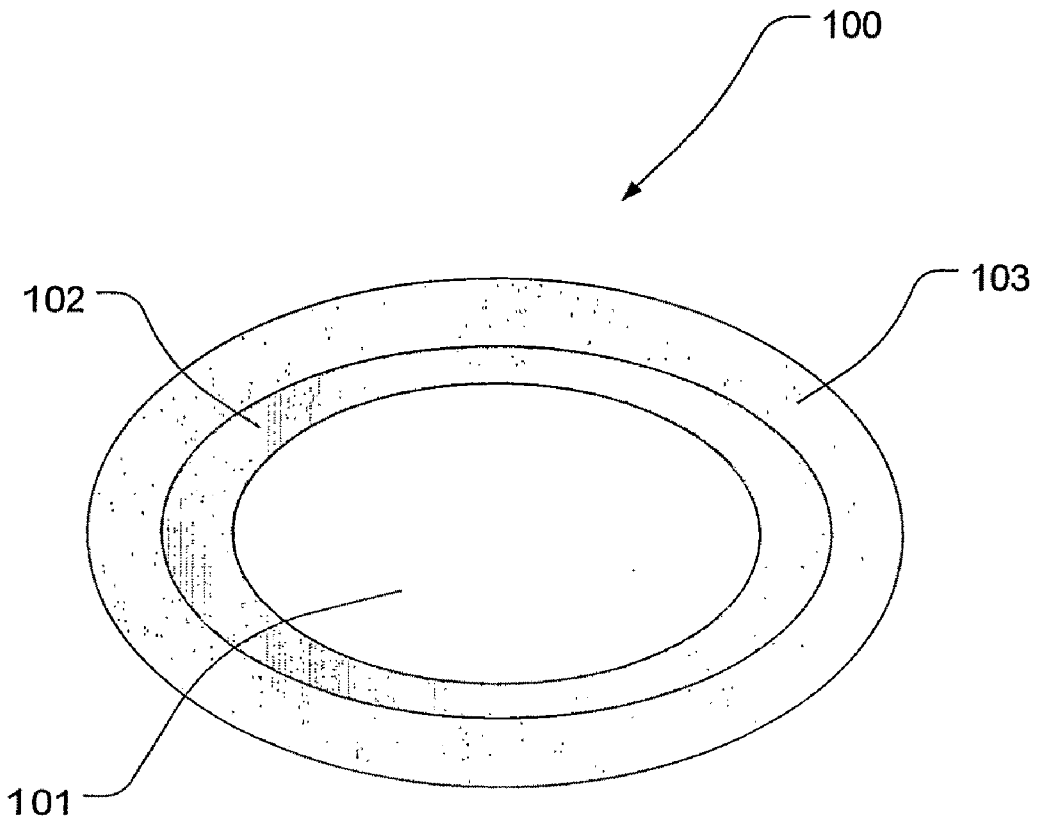
FIG. 1A depicts a schematic of an exemplary two-layer coating drug design.

To provide an overall understanding, certain illustrative practices and embodiments will now be described, including a composition and method for inhibiting, preventing, or ameliorating complications associated with ingestion of a medicinal, chemical, and/or biological substance or agent. For convenience, in lieu of the terminology "a medicinal, chemical, and/or biological substance or agent," the phrases "therapeutic substance," "therapeutic compound," and "pharmaceutically active agent" are sometimes generically, and interchangeably, employed herein. However, it is understood that the scope of the application is not limited to therapeutic substances alone, and that included within the scope of the compositions and methods described herein are embodiments wherein the material whose dosage is to be regulated contains a combination of at least one chemical, biological, and/or biochemical substance or agent primarily intended for non-therapeutic, non-pharmacological, or even non-oral use.

In a typical embodiment, the therapeutic substance includes a pharmacological compound, for example, a drug (including chemical drugs and biologics) for treating an underlying disease, ailment, or other medical condition. Examples of a pharmacological compound (or a pharmaceutically active agent) include, without limitation, a pain reliever such as acetaminophen, an anti-inflammatory drug such as ibuprofen, an anti-psychotic drug (neuroleptic) such as risperidone or clozapine, and a host of other chemical and/or biological compounds or agents (including, for example, biochemical compounds or agents).

In such therapeutic or pharmacological applications, the composition formulated by the compositions and methods described herein typically includes a dosage form suitable for oral administration. For example, and without limitation, the dosage form can be a combination of one or more of a tablet, a capsule, a sprinkle, a caplet, a multi-particulate formulation (e.g., granules, spheroids, ellipsoids, beads, pellets, or a combination of these), a chewing gum, a lozenge, and a crystal. The generic term "pill" is employed herein to generically refer to an embodiment of the dosage form. The pill can include a gelatin coating or a coating made of a gelatinous or gelatin-like substance.

In one aspect, the compositions and methods described herein reduce the toxicity of chemical substances and/or biological agents down to safe levels by inducing diarrhea in a specimen. Characteristic aspects of the diarrhea include, but are not limited to, chronic and/or at least one episodic occurrence of increased stool production, for example, increased stool mass, increased water or other fluid content associated with the stool, or a combination thereof. Typically, diarrhea is associated with abnormally frequent bowel movements that produce intestinal evacuations of increased- or possibly, though less typically, reduced-fluidity. Intestinal evacuations include, for example and without limitation, fecal matter typically discharged through the anus or other exit port and/or tubular means (for receiving and/or collecting bodily excrements) connected to an intestinal, post-intestinal, or distal portion of the alimentary canal.

The term "specimen" or "subject" as used herein, typically refers to a human subject. However, it is understood that the scope of the application is not limited to human specimens, and that other animals having a digestive system that includes a stomach or stomach-like organ and one or more intestines or intestine-like organs are within the scope of the compositions and methods described herein. For example, and without limitation, specimens within the scope of the application include primates, cattle, other domesticated or wild mammalians, or a combination of these.

FIG. 1A depicts a schematic representation of an exemplary composition 100 according to an embodiment of the application. In the embodiment depicted in FIG. 1A, the dosage form 100 is a tablet, capsule, caplet, or another orally administrable dosage form-generically referred to herein as a pill.

In the illustrated embodiment, the inner core 101 contains at least one therapeutic substance, for example and without limitation, a pharmaceutically active compound. The core 101 is coated by, covered by, enveloped by, immersed in, encapsulated in, or otherwise embedded in a layer 102 containing at least one (typically active) diarrhea-inducing substance. The amount of the diarrheagenic substance used in layer 102 is a function of one or more salient traits of members of the target specimen population (e.g., weight, height, gender, gastro-intestinal or other traits of the specimen population), potency and efficacy of the diarrheagenic substance 102, potency and/or toxicity of the therapeutic substance in the core 101, or other variables.

According to one practice, the pill 100 is uncoated (i.e., it has no layer 103). According to an alternative practice, a portion (more typically, the entirety) of an outer surface of the pill includes a coating 103 applied by any of a number of known techniques. The coating layer 103 performs one or more of the following functions, among others: (a) it protects either or both of the therapeutic and diarrhoetic contents of the composition 100 (e.g., by discouraging, reducing, or in some instances, preventing, premature absorption and/or disintegration of the contents in the body of the specimen); (b) it improves the visual or other physical attributes of the pill, for aesthetic or other reasons; and (c) it carries one or more functional characteristics (e.g., pharmacological traits) of the pill.

In one aspect, the compositions and methods described herein discourage, substantially reduce, or in some instances prevent, absorption-in the stomach of the therapeutic composition present in the core 101 and/or the diarrheagenic substance or agent present in the diarrhoetic layer 102. According to one practice, the compositions, compositions, and methods described herein accomplish this at least in part by employing an enteric material in the layer 103 to encapsulate the diarrhea-inducing compound 102 and the therapeutic substance 101. The enteric material discourages, or more typically prevents, the diarrhoetic coating and the therapeutic substance 101 from being inactivated by the acidity of the gastric environment. Layer 103 may include one or more suitable hydrophilic polymers; enteric polymer coating materials; and/or suitable pH modifiers.

According to a typical practice, layer 103 serves as an effective controlled release coating when ingested, contacted, or otherwise exposed to an environmental fluid such as, for example and without limitation, a gastric fluid or another dissolution medium in the GI tract.

Among the characteristics of a typical enteric coating material are that (a) it passes through the stomach substantially unaltered; and (b) it begins to disintegrate approximately upon or after reaching the small intestine. This is possible at least in part because the enteric material resists the acidity of gastric fluids and does not disintegrate until essentially on or after entry into the environment of the small intestine where the pH levels exceed those of the gastric fluids. In a typical embodiment, the enteric material is designed, configured, adapted, or otherwise selected to resist pH levels up to about 5.5 and to commence rapid disintegration when pH levels of its surroundings exceed about 5.5. The enteric coating 103 can be designed to disintegrate if exposed to an environment characterized by any of a number of pH levels, so that the diarrheagenic substance and therapeutic substance can be targeted for absorption at certain segments of the small intestine-such as the duodenum, jejunum, or ileum; or the colon. Absorption is designed to occur based on a particular order, the diarrheagenic substance being the first to disintegrate and be absorbed at approximately a first location in the small intestine, followed by the therapeutic substance, which is absorbed at approximately a second, subsequent location in the small or large intestine.

The acidity of the internal environment of the stomach of a human specimen, for example, is generally a function of at least the amount or type of food content in the stomach, and can be as low as about 1 pH (very acidic) and as high as about 4 pH. The alkalinity of the internal environment of the small intestine of a human specimen is typically about 8 pH.

Once in the small or large intestine, the diarrhoetic coating 102 dissolves and binds to appropriate receptors in the GI tract. The diarrhea induced by the compositions, compositions, and methods described herein typically reverses fluid absorption and causes rapid expulsion of the GI tract's solid, fluid, and/or other contents. Accordingly, this process reduces, or in some instances prevents, absorption of the therapeutically-active compound that is coated by the diarrheagenic substance. According to one practice, the diarrhoetic layer 102 includes one or more suitable pH modifiers. A pH modifier may serve to modify the pH of the local environment so that the disintegration kinetics of a pH dependent enteric coating are dependent not only on the specimen's physiology but also on the number of pills ingested. An alternative, or additional, function of a pH modifier is to modulate the biological activity, potency, or efficacy of a diarroetic substance.

According to a typical practice, the amount of the diarrhoetic compound in each dosage form is insufficient to produce diarrhea in a typical member of a broad specimen population (e.g., in a typical human patient). However, if several pills (constructed according to the compositions and methods described herein) are ingested within a sufficiently short time interval-such that the cumulative intake of the diarrhea-inducing substance exceeds a recommended amount or a threshold dosage-rapid and severe diarrhea ensues.

Figure 1B:
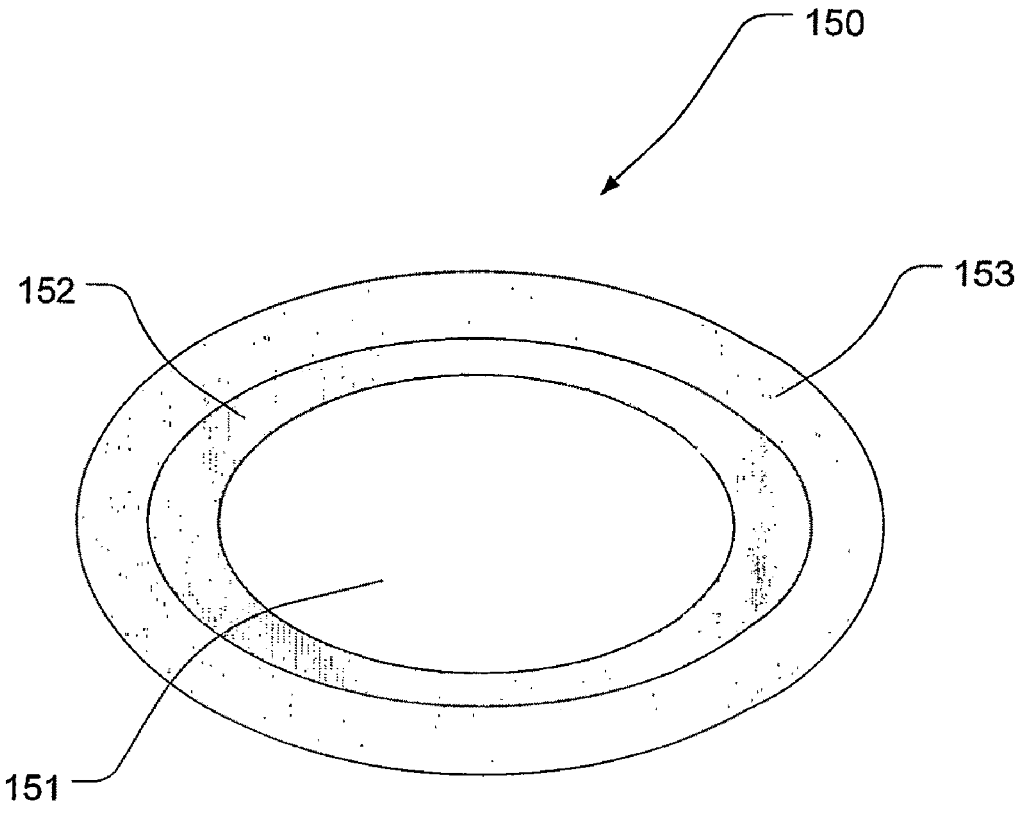
FIG. 1B depicts a schematic of another exemplary two-layer coating drug design.

FIG. 1B depicts a schematic representation of another exemplary composition 150 according to an embodiment of the application. Layer 153 includes one or more diarrhea-inducing substances substantially equivalent to the one or more diarrheagenic substances of layer 102 depicted in FIG. 1A. According to one practice, the coating layer 152 regulates the availability of the therapeutic substance 151 at least in part by controlling the release of the therapeutic substance in the body of the specimen (e.g., this is variously known as a modified-release or controlled-release mechanism). The coating layer 152 may be designed to have a pH-dependent disintegration property, as described above in relation to the enteric coating 103 of FIG. 1A, for example.

Alternatively, or additionally, the compositions and methods described herein may design one or more characteristics of layer 152 (e.g., a thickness of layer 152, and/or a chemical, biological, biochemical, electrostatic, or other physical property of layer 152) to adjust the time at which, or time interval during which, layer 152 disintegrates, thereby exposing and releasing the therapeutic substance 151 at a desired location in the small or large intestine and at an appropriate time instance or time interval.

Figure 2:
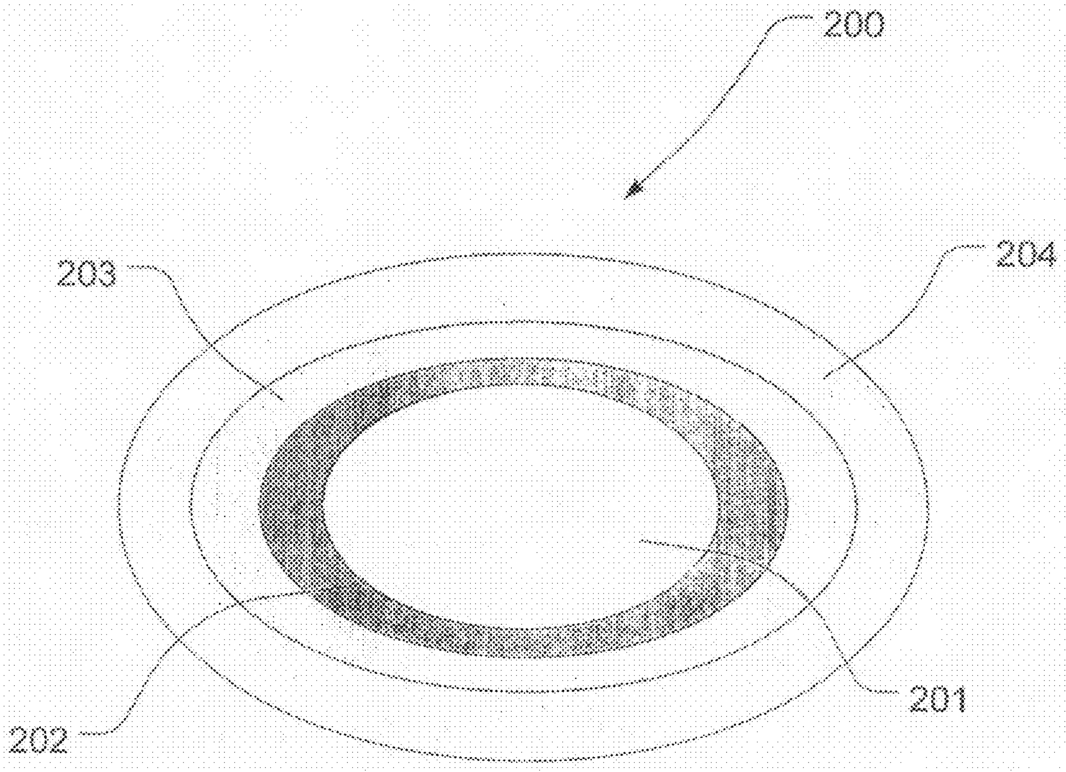
FIG. 2 depicts a schematic of an exemplary three-layer coating drug design according.

FIG. 2 depicts a schematic representation of another exemplary composition 200 according to an embodiment of the application. The composition 200 includes features described above in relation to FIGS. 1A-1B. In particular, composition includes a core 201 that contains the therapeutic substance. The core 201 is coated by layer 202 which is substantially similar to the time-delay layer 152 described above in relation to FIG. 1B and controls the amount and timing of the release of the therapeutic substance in the core 201.

Layer 203 contains the diarrheagenic substance. This layer is substantially the same as layer 102 of FIG. 1A or layer 153 of FIG. 1B. Layer 204 contains an enteric coating substantially the same as layer 103 described in relation to FIG. 1A. The composition 200, therefore, incorporates various protective tiers of the embodiments of FIGS. 1A-1B.

Figure 3:
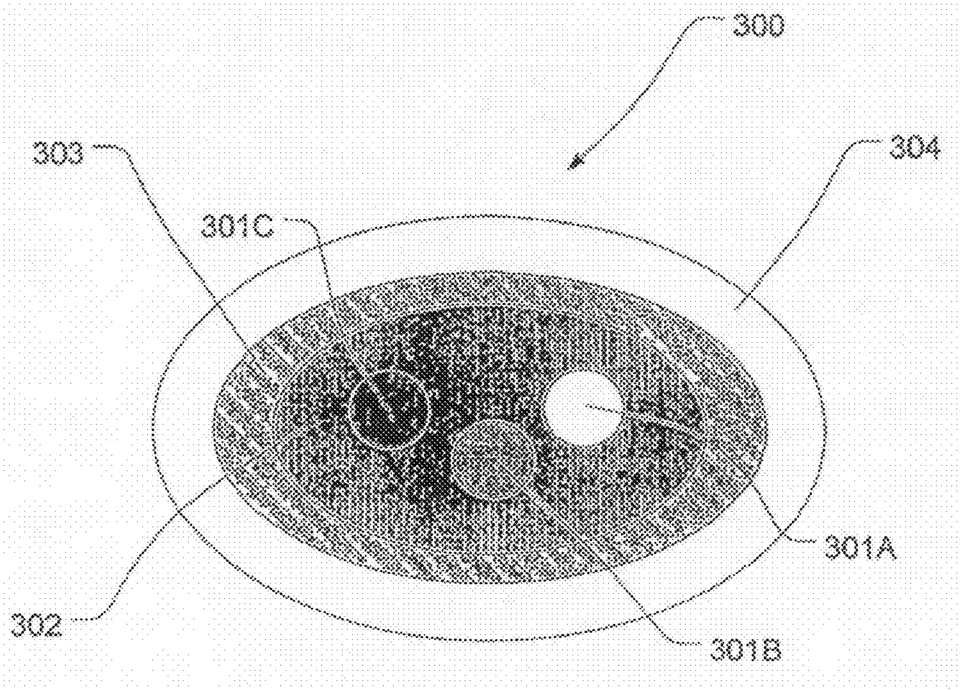
FIG. 3 depicts a schematic of an exemplary multiparticulate three-layer coating drug design.

FIG. 3 depicts a schematic representation of another exemplary composition 300 according to a multi-particulate embodiment of the application. According to various practices, each particulate is in the form of a granule, a spheroid (e.g., a microsphere), a bead, a pellet, an ellipsoid, or a microcapsule.

In FIG. 3, three therapeutic cores 301A-301C are depicted, though it should be noted that a multi-particulate formulation may include as few as two such cores. Each of the therapeutic cores 301A-301C is analogous to one or more of the cores 101, 151, and 201 of FIGS. 1A, 1B, and 2, respectively, and contains one therapeutic substance or a mixture of two or more therapeutic substances. The contents or even the particulate shapes of the therapeutic cores 301A-301C may be essentially mutually identical or different at least between two particulates. For example, and without limitation, core 301A may contain a first therapeutic substance, core 301B may contain a second therapeutic substance different from the first therapeutic substance, and core 301C may contain a third therapeutic substance different from each of the first and second therapeutic substances. Alternatively, at least one of the particulates 301A-301C may contain a mixture of two or more therapeutic substances, wherein the mixture is different from the contents of at least one other of the particulates 301A-301C. Similar remarks apply to the shapes of each of the particulates 301A-301C, wherein they may all be identical (e.g., all may be spherical of the same size) or at least one may have a shape different from others (it may be ellipsoidal whereas the others are spherical, or it may be spherical but larger than the other spherical particulates). Various permutations of how one or more therapeutic substances may be distributed among the two or more particulate cores (such as 301A-301C), as well as various permutations of how the particulates are shaped or sized, are within the scope of the compositions and methods of the application.

In the embodiment depicted in FIG. 3, layer 304 includes an enteric coating substantially similar to the coating layer 103 as described in relation to FIG. 1A or coating layer 204 as described in relation to FIG. 2. Layer 304 coats the diarrhea-inducing substance layer 303, which includes one or more diarrhea-inducing substances similar to layer 102 of FIG. 1A or layer 203 of FIG. 2.

Coating 302 includes a time-delay or release-control substance similar to what was described in relation to layer 152 or layer 202 of FIG. 1B and FIG. 2, respectively. According to one practice, one or more of the therapeutic cores 301A-301C include an inert pharmaceutical bead that at least partially defines the core 101 of FIG. 1A, core 151 of FIG. 1B, or core 201 of FIG. 2. An example of such a bead is a NU-PAREIL® bead (Sugar Spheres NF) (registered to Sucrest Corporation), which is a dry, free-flowing, spherical product containing sugar and starch for use as a base upon which drugs or medications are deposited in the manufacture of pharmaceutical preparations.

The resultant controlled-release bead or beads in cores 301A-301C (which are typically, though not necessarily, essentially solid) may be enclosed by the coating 302 (which may be gelatinous or gelatin-like) in an amount sufficient to provide an effective controlled-release dose when ingested, contacted, or otherwise exposed to an environmental fluid such as, for example and without limitation, a gastric fluid or another dissolution medium in the GI tract.

The controlled-release formulation embodiment of the compositions, compositions, and methods described herein progressively releases the therapeutically-active agent upon ingestion and/or exposure to gastric fluids and, subsequently, intestinal fluids. The controlled-release profile of the formulations of the application may be altered, for example, by varying the amount of the enteric coating material in layer 302; varying relative amounts of plasticizers; incorporating additional ingredients or excipients (e.g., in layer 302); altering the method of manufacture; etc. The dissolution profile of the ultimate product may also be modified, for example, by increasing or decreasing the thickness of a retardant in one or more of the coating layers 302 and 304 of FIG. 3.

Figure 4:
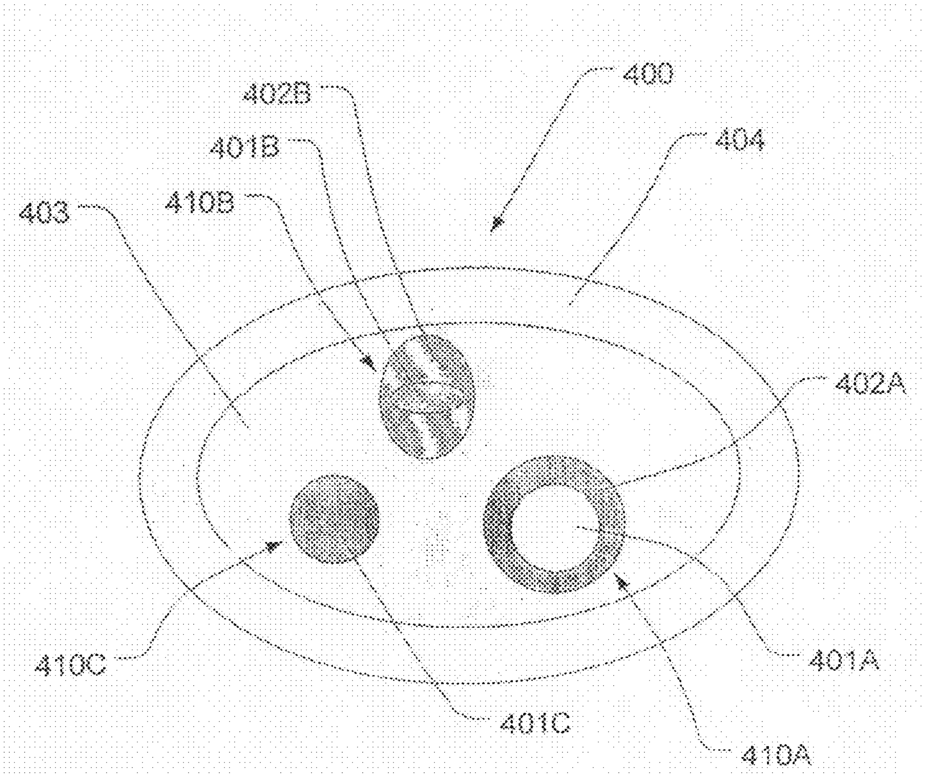
FIG. 4 depicts a schematic of a multiparticulate drug design showing various combinations of particulate types.

Turning to FIG. 4, a dosage form 400 is depicted which includes another multi-particulate formulation according to an exemplary embodiment of the application. As was described in relation to FIG. 3, at least one particulate may be in the form of a granule, a spheroid (e.g., a microsphere), a bead, a pellet, an ellipsoid, or a microcapsule.

One or more therapeutic substances are present in the dosage form 400 depicted in FIG. 4. In the particular embodiment of FIG. 4, a first particulate 410A is shown which includes a first therapeutic substance in a first core 401A having a first coating 402A. The coating is made at least in part (though typically, essentially) of a first time-delay or controlled-release material not unlike coating 152 of FIG. 1B, coating 202 of FIG. 2, or coating 302 of FIG. 3.

An optional, second particulate 410B includes a second therapeutic substance 401B coated by a second coating 402B, the second coating made at least in part (though typically, essentially) of a second time-delay or controlled release material. According to various practices, the first and second cores 401A and 401B contain essentially identical therapeutic substances or essentially distinct therapeutic substances. Also according to various practices, the first and second coatings 402A and 402B contain essentially identical time-delay or controlled-release substances or essentially distinct time-delay or controlled release substances.

Optionally, the dosage form 400 of FIG. 4 contains a particulate 410C made, at least in part, of a therapeutic substance 401C (and having essentially no diarrhea-inducing coating or time-delay or controlled-release coating). The therapeutic substance 401C may have a constitution (and at least one associated property) essentially distinct from those of each of the therapeutic substances in the first and second cores 401A and 401B.

Alternatively, the therapeutic substance 401C may be essentially identical in constitution (and in at least one associated biological, chemical, biochemical, physical, biophysical, and/or other salient characteristic) to those of at least one of the first and second therapeutic substances in the respective cores 401A and 401B.

The relative amounts of the time-delay or controlled-release compounds in the particulates 410A and 410B may vary; the amounts need not be essentially identical. The relative sizes and/or shapes of the particulates 410A-410C may vary; the sizes and/or shapes need not all be essentially identical.

In the embodiment depicted in FIG. 4, layer 404 includes an enteric coating substantially similar to the coating layer 103 as described in relation to FIG. 1A, coating layer 204 as described in relation to FIG. 2, or coating layer 304 as described in relation to FIG. 3. Layer 404 coats the diarrhea-inducing substance in 403, which includes one or more diarrhea-inducing substances similar to layer 102 of FIG. 1A, layer 203 of FIG. 2, or layer 303 of FIG. 3.

Figure 5:
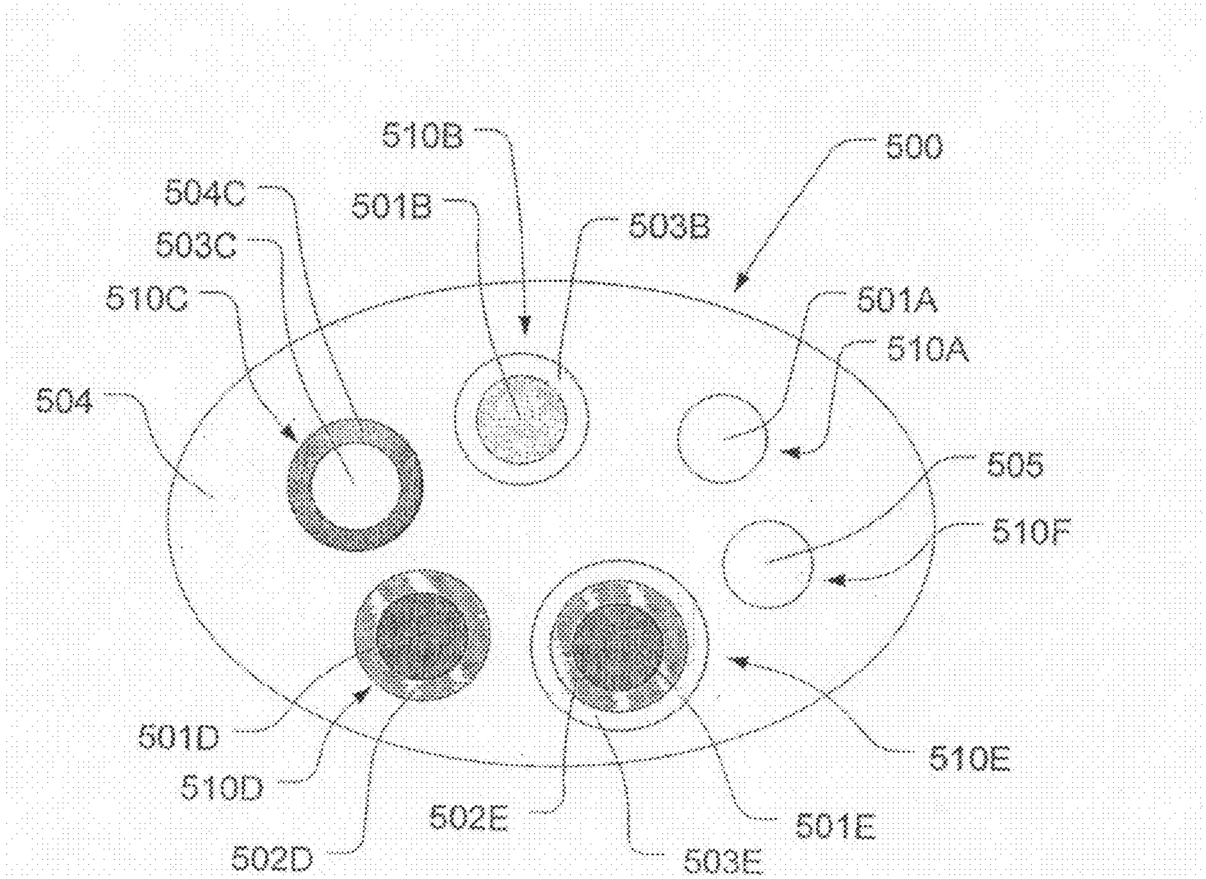
FIG. 5 depicts a schematic embodiment of yet another multiparticulate drug design.

Turning to FIG. 5, an embodiment is depicted showing various configuration permutations that the therapeutic, diarrheagenic, and time-delay or controlled-release substances, agents, or compounds may have in an exemplary multi-particulate composition 500. In particular, FIG. 5 shows that the therapeutic agent and the diarrheagenic substance can be present in the same or in different, separate, or otherwise distinct particulates. For example, FIG. 5 depicts: (a) a population of at least one particulate 510A containing a therapeutic substance 501A but essentially no diarrheagenic, time-delay, or controlled-release substance; (b) a population of at least one particulate 510C containing a diarrheagenic substance 503C and having an optional enteric coating 504C; and (c) a population of at least one particulate 510F containing a mixture 505 of a therapeutic substance and a diarrheagenic substance. An optional enteric coating (not shown in the figure) analogous to 504C may be applied to the therapeutic particulate 510A.

Also depicted in FIG. 5 is a population of at least one particulate 510B containing a therapeutic core 501 B coated by a diarrheagenic layer 503B but essentially no time-delay or controlled-release substance. Particulate 510B is similar in constitution to the composition 100 depicted in FIG. 1A.

The embodiment of FIG. 5 also shows a population of at least one particulate 510D containing a therapeutic core 501D coated by a time-delay or controlled-release layer 502D but essentially no diarrheagenic substance. Particulate 510D is similar in constitution to the composition 150 depicted in FIG. 1B.

FIG. 5 also depicts a population of at least one particulate 510E containing a therapeutic core 501E coated by a time-delay or controlled-release substance 502E, which is in turn coated by a diarrheagenic layer 503E. Particulate 510E is similar in constitution to the composition 200 depicted in FIG. 2.

The coating 504 includes the inert coating discussed above in relation to the previous figures. In the embodiment depicted in FIG. 5, coating 504 includes an enteric substance substantially similar to the coating layer 103 as described in relation to FIG. 1A, coating layer 204 as described in relation to FIG. 2, coating layer 304 as described in relation to FIG. 3, or coating layer 404 as described in relation to FIG. 4.

As is the case with the embodiments shown in the previous figures, the therapeutic, time-delay or controlled-release, or diarrhea-inducing substances in one particulate may have a constitution (and at least one associated biological, chemical, biochemical, physical, biophysical, or other salient characteristic) essentially distinct from or essentially identical to those of a counterpart substance in another particulate. For example, and without limitation, a diarrheagenic substance in a first particulate may be essentially identical to or different from a diarrheagenic substance in a second particulate; and/or a pH dependent enteric coating in a first particulate may disintegrate at a pH level that is at least approximately identical to or essentially different from that at which an enteric coating in a second particulate disintegrates.

According to a typical practice, the diarrheagenic substance (e.g., *Escherichia coli* Heat Stable Enterotoxin (STa)) is introduced into the composition 500 such that the amount of the diarrheagenic substance is insufficient to cause diarrhea when the medication is taken at an appropriate level, typically below or at about a recommended or threshold level. However, an excessive intake of the therapeutically-active compound causes a rapid diarrhea that expels the toxic or harmful accumulation of the therapeutic substantially before it causes significant injury, death, or other harm to the specimen.

The different populations can then be mixed in the desired ratios before being filled into a final dosage form 500 such as a tablet, caplet, capsule, sprinkle, or a pill-like orally-administrable formulation described above.

The release kinetics of the particulates may also be different such that the particulates containing the diarrheagenic substances release the diarrheagenic substance into the small or large intestine prior to the therapeutic compound being released by other particulates. The time between the commencement of release of the diarrheagenic substance and the therapeutic compound can vary. The compositions and methods described herein adjust the time to be sufficiently long to allow for severe diarrhea to develop (for example, in a patient who has overdosed on a medication) and hence expel the therapeutic compound from the GI tract prior to its absorption into the blood stream.

According to yet another embodiment, one or more populations of particulates exist that contain both the therapeutic compound and the diarrheagenic agent. According to one practice, in particles that contain both the diarrheagenic agent and the therapeutic compound, the particles are coated on their outer-most surface with the diarrheagenic agent to ensure that the diarrheagenic substance is released into the small or large intestine prior to the therapeutic compound is released. Such populations of particles can be mixed together prior to being filled into a final dosage form, such as a capsule or sprinkle, or they can be mixed with one or more populations that contain the therapeutic compound but not the diarrheagenic agent and/or the diarrheagenic agent but not the therapeutic compound prior to being filled into a final dosage form such as a capsule or a sprinkle.

According to one practice, the dosage form is adapted to have a modified release property. The term "modified release," as defined herein, refers to the release of the therapeutic compound at a rate such that the plasma concentration of the therapeutic compound within the person to whom the therapeutic compound has been administered is maintained within an acceptable therapeutic range, that is, above a minimum therapeutically-effective concentration, but below toxic levels, over the period of time in which the therapeutic compound is released.

The compositions and methods described herein provide the modified-release property of the oral dosage form in any of a number of ways. For example, and without limitation, a modified-release carrier can be used that is incorporated into the matrix of the composition. Alternatively, or additionally, a modified-release coating may be applied to a surface of the dosage form. In embodiments that employ a modified-release coating, the coating material is selected to achieve the desired in vitro release rate and, typically, is capable of forming a strong, continuous film that is smooth and elegant, and is able to support colorants and other coating additives. Additionally, the coating material has little or substantially no toxicity, is substantially inert, and/or is substantially tack-free.

While the therapeutic compound may have a modified-release property in the small and/or large intestines, the diarrheagenic substance can be packaged in a modified-release form or in an immediate-release form for when it reaches the small or large intestine. In a typical embodiment, the therapeutic compound has a coating to reduce, or in some instances substantially prevent, the absorption and/or degradation of the diarrheagenic substance in the stomach. In a typical embodiment, the coating also substantially reduces, or in some instances prevents, the absorption of the therapeutic compound in the stomach.

In another embodiment, the modified-release coating permits either pH dependent or pH-independent release of the therapeutic compound and/or the diarrheagenic substance, for example and without limitation, when exposed to the gastrointestinal liquids. A pH-dependent coating serves to release the therapeutic compound in desired locations of the GI tract for example, the stomach, small intestine, or colon-providing an absorption profile capable of inducing in the user a sustained release of opiate, for example, at least about 1 hour up to about 30 hours. When a pH-independent coating is desired, the coating is designed to achieve optimal release regardless of pH variations along the GI tract. In yet another embodiment, a composition is formulated that releases a portion of the unit dose in one desired location of the GI tract (e.g., the stomach) and releases the remainder of the unit dose in another location of the GI tract (e.g., the small intestine).

The application also contemplates a composition comprising an agent that would deter tempering or breaking of the pharmaceutical composition to cause release of one or more pharmaceutically active agents included therein. Such an agent can be an irritant, such as for example, an irritant added to prevent someone from crushing a pill of an extended-release formulation and thereby destroying its extended-release characteristics as described in U.S. Patent Application Publication No. 20030125347. Examples of suitable local irritants may be of natural or synthetic origin and include mustard and derivatives of mustard, for example, allyl isothiocyanate and p-hydroxybenzyl isothiocyanate; capsaicinoids such as capsaicin, dihydrocapsaicin, nordihydrocapsaicin, homocapsaicin, and homodihydrocapsaicin; mint; aspirin; and acids such as acids with one or more carboxyl moieties such as formic acid, acetic acid, propionic acid, butyric acid, valeric acid, caproic acid, caprilic acid, capric acid, oxalic acid, malonic acid, succinic acid, glutaric acid, adipic acid, maleic acid, fumaric acid, and citric acid. Preferred local irritants for use in the present application are capsaicinoids such as, for example, capsaicin.

Exemplary Pharmaceutically Active Agents or Substances

According to one practice, a therapeutic substance according to the compositions, compositions, and methods described herein includes one or more compounds suitable or otherwise used for the treatment, prophylaxis, cure, or mitigation of a disease in humans, other mammalians, or living beings having a gastro-intestinal system analogous to those of humans or other mammalians. Exemplary therapeutically-active substances include, without limitation, one or more of: antifungal agents, antibacterial agents, antimicrobial agents, antiviral agents, spermicides, hormone agents, antitrichomonial agents, antiprotozoan agents, antimycoplasm agents, antiretroviral agents, nucleoside analogues, reverse transcriptase inhibitors, protease inhibitors, contraceptive agents, sulfadrugs, sulfonamides, sulfones, hygiene agents, probiotic agents, vaccine agents, antibody agents, peptide agents, protein agents, polysaccharide agents, nucleic acids, plasmids, liposomes, carbohydrate polymers, transgenic bacteria, yeast, chemotherapeutic agents, steroid agents, growth-enhancing agents, libido enhancers, androgenic substances, chitin derivatives, dietary supplements, and mixtures and combinations thereof.

In an exemplary embodiment, acetaminophen is used as a therapeutically active substance. The amount of acetaminophen included in each pill is typically about 500 milligrams (mg). According to another practice, the amount of acetaminophen included in each pill is about 100 mg. According to another practice, the amount of acetaminophen included in each pill is about 200 mg. According to another practice, the amount of acetaminophen included in each pill is about 300 mg. According to another practice, the amount of acetaminophen included in each pill is about 400 mg.

In an exemplary embodiment, the enteric coating is based on the use of gelatin. One or more pH sensitive properties of a gelatin-based enteric coating can be modified using known methods. The amount of enteric coating can be modified to meet the desired release kinetics in the small or large intestine. According to another practice, the enteric coating includes EUDRAGIT-S100® (Acrylates Copolymer) using methods similar to those described, for example, in U.S. Pat. No. 6,897,205.

A number of active pharmaceutical ingredients which are to be released in the small intestine or large intestine are suitable for use by the compositions, compositions and methods described herein. Examples of such pharmaceutical ingredients include, for example and without limitation: antidiabetics, analgesics, antiinflammatory agents, antirheumatics, antihypotensive agents, antihypertensive agents, psychoactive drugs, tranquillizers, antiemetics, muscle relaxants, glucocorticoids, agents for treating an inflammatory bowel disease (e.g., ulcerative colitis, Crohn's disease, etc.), antiallergics, antibiotics, antiepileptics, anticoagulants, antimycotics, antitussives, arteriosclerosis remedies, diuretics, proteins, peptides, enzymes, enzyme inhibitors, gout remedies, hormones and inhibitors thereof, cardiac glycosides, immunotherapeutic agents and cytokines, laxatives, lipid-lowering agents, migraine remedies, mineral products, otologicals, anti-Parkinson agents, thyroid therapeutic agents, spasmolytics, platelet aggregation inhibitors, vitamins, cytostatics and metastasis inhibitors, phytopharmaceuticals, chemotherapeutic agents and amino acids.

Examples of suitable active ingredients include but are not limited to acarbose, antigens, beta-receptor blockers, non-steroidal antirheumatia, cardiac glycosides, acetylsalicylic acid, virustatics, aclarubicin, acyclovir, cisplatin, actinomycin, alpha- and beta-sympatomimetics, (dmeprazole, allopurinol, alprostadil, prostaglandins, amantadine, ambroxol, amlodipine, methotrexate, Saminosalicylic acid, amitriptyline, amoxicillin, anastrozole, atenolol, azathioprine, balsalazide, beclomethasone, benzodiazepine, betahistine, bezafibrate, bicalutamide, diazepam and diazepam derivatives, budesonide, bufexamac, buprenorphine, methadone, calcium salts, potassium salts, magnesium salts, candesartan, carbamazepine, captopril, cefalosporins, cetirizine, chenodeoxycholic acid, ursodeoxycholic acid, theophylline and theophylline derivatives, trypsins, cimetidine, clarithromycin, clavulanic acid, clindamycin, clobutinol, clonidine, cotrimoxazole, codeine, caffeine, vitamin D and derivatives of vitamin D, colestyramine, cromoglicic acid, coumarin and coumarin derivatives, cysteine, cytarabine, cyclophosphamide, ciclosporin, cyproterone, cytarabine, dapiprazole, desogestrel, desonide, dihydralazine, diltiazem, ergot alkaloids, dimenhydrinate, dimethyl sulphoxide, dimeticone, dipyridarnoi, domperidone and domperidan derivatives, dopamine, doxazosin, doxorubizin, doxylamine, dapiprazole, benzodiazepines, diclofenac, glycoside antibiotics, desipramine, econazole, ACE inhibitors, enalapril, ephedrine, epinephrine, epoetin and epoetin derivatives, morphinans, calcium antagonists, irinotecan, modafinil, orlistat, peptide antibiotics, phenyloin, riluzoles, risedronate, sildenafil, topiramate, macrolide antibiotics, oestrogen and oestrogen derivatives, progestogen and progestogen derivatives, testosterone and testosterone derivatives, androgen and androgen derivatives, ethenzamide, etofenamate, etofibrate, fenofibrate, etofylline, etoposide, famciclovir, famotidine, felodipine, fenofibrate, fentanyl, fenticonazole, gyrase inhibitors, fluconazole, fludarabine, fluarizine, fluorouracil, fluoxetine, flurbiprofen, ibuprofen, flutamide, fluvastatin, follitropin, formoterol, fosfomicin, furosemide, fusidic acid, gallopamil, ganciclovir, gemfibrozil, gentamicin, ginkgo, Saint John's wort, glibenclamide, urea derivatives as oral antidiabetics, glucagon, glucosamine and glucosamine derivatives, glutathione, glycerol and glycerol derivatives, hypothalamus hormones, goserelin, gyrase inhibitors, guanethidine, halofantrine, haloperidol, heparin and heparin derivatives, hyaluronic acid, hydralazine, hydrochlorothiazide and hydrochlorothiazide derivatives, salicylates, hydroxyzine, idanibicin, ifosfamide, imipramine, indometacin, indoramine, insulin, interferons, iodine and iodine derivatives, isoconazole, isoprenaline, glucitol and glucitol derivatives, itraconazole, ketoconazole, ketoprofen, ketotifen, lacidipine, lansoprazole, levodopa, levomethadone, thyroid hormones, lipoic acid and lipoic acid derivatives, lisinopril, lisuride, lofepramine, lomustine, loperamide, loratadine, maprotiline, mebendazole, mebeverine, meclozine, mefenamic acid, mefloquine, meloxicam, mepindolol, meprobamate, meropenem, mesalazine, mesuximide, metamizole, metformin, methotrexate, methylphenidate, methyl prednisolone, metixene, metoclopramide, metoprolol, metronidazole, mianserin, miconazole, minocycline, minoxidil, misoprostol, mitomycin, mizolastine, moexipril, morphine and morphine derivatives, evening primrose, nalbuphine, naloxone, tilidine, naproxen, narcotine, natamycin, neostigmine, nicergoline, nicethamide, nifedipine, niflumic acid, nimodipine, nimorazole, nimustine, nisoldipine, adrenaline and adrenaline derivatives, norfloxacin, novamine sulfone, noscapine, nystatin, ofloxacin, olanzapine, olsalazine, omeprazole, omoconazole, ondansetron, oxaceprol, oxacillin, oxiconazole, oxymetazoline, pantoprazole, paracetamol, paroxetine, penciclovir, oral penicillins, pentazocine, pentifylline, pentoxifylline, perphenazine, pethidine, plant extracts, phenazone, pheniramine, barbituric acid derivatives, phenylbutazone, phenyloin, pimozide, pindolol, piperazine, piracetam, pirenzepine, piribedil, piroxicam, pramipexole, pravastatin, prazosin, procaine, promazine, propiverine, propranolol, propyphenazone, prostaglandins, protionamide, proxyphylline, quetiapine, quinapril, quinaprilat, ramipril, ranitidine, reproterol, reserpine, ribavirin, rifampicin, risperidone, ritonavir, ropinirole, roxatidine, roxithromycin, ruscogenin, rutoside and rutoside derivatives, sabadilla, salbutamol, salmeterol, scopolamine, selegiline, sertaconazole, sertindole, sertralion, silicates, sildenafil simvastatin, sitosterol, sotalol, spaglumic acid, sparfloxacin, spectinomycin, spiramycin, spirapril, spironolactone, stavudine, streptomycin, sucralfate, sufentanil, sulbactam, sulphonamides, sulfasalazine, sulpiride, sultamicillin, sultiam, sumatriptan, suxamethonium chloride, tacrine, tacrolimus, taliolol, tamoxifen, taurolidine, tazarotene, temazepam, teniposide, tenoxicam, terazosin, terbinafine, terbutaline, terfenadine, terlipressin, tertatolol, tetracyclins, teryzoline, theobromine, theophylline, butizine, thiamazole, phenothiazines, thiotepa, tiagabine, tiapride, propionic acid derivatives, ticlopidine, timolol, tinidazole, tioconazole, tioguanine, tioxolone, tiropramide, tizanidine, tolazoline, tolbutamide, tolcapone, toinaftate, tolperisone, topotecan, torasemide, antioestrogens, tramadol, tramazoline, trandolapril, tranylcypromine, trapidil, trazodone, triamcinolone and triamcinolone derivatives, triamterene, trifluperidol, trifluridine, trimethoprim, trimipramine, tripelennamine, triprolidine, trifosfamide, tromantadine, trometamol, tropalpin, troxerutine, tulobuterol, tyramine, tyrothricin, urapidil, ursodeoxycholic acid, chenodeoxycholic acid, valaciclovir, valproic acid, vancomycin, vecuronium chloride, Viagra, venlafaxine, verapamil, vidarabine, vigabatrin, viloazine, vinblastine, vincamine, vincristine, vindesine, vinorelbine, vinpocetine, viquidil, warfarin, xantinol nicotinate, xipamide, zafirlukast, zalcitabine, zidovudine, zolnitriptan, zolpidem, zoplicone, zotipine and the like.

Exemplary Diarrheagenic Substances or Agents

The diarrhea-inducing substances referred to in the descriptions of FIG. 1A-FIG. 5 typically include one or more of a bacterial toxin (e.g., *Escherichia coli* Heat Stable Enterotoxin (STa)); a viral protein; a protein and/or peptide (e.g., guanylin and uroguanylin); a laxative (e.g., aloe vera, bisacodyl, casanthranol, cascara sagrada, castor oil, dehydrocholic acid, phenolphthalein, picosulfate, senna and sennosides); and another naturally-occurring or synthetic pharmacological compound having a diarrheagenic property or capable of inducing diarrhea in a subject or specimen.

Examples of enterotoxins are listed as follows:

| | 1 5 10 15 18 |
|---|---|
| SEQ ID NO: 1 (Ec-STp) | NTFYCCEL CCNPACA GCY |
| SEQ ID NO: 2 (Ec-STh) | NSSNYCCEL CCNPACT GCY |
| SEQ ID NO: 3 (Vc-01-ST) | FIKQVDENGNLIDCCEI CCNPACF GCLN |
| SEQ ID NO: 4 (Vc-n-01-ST) | IDCCEI CCNPACF GCLN |
| SEQ ID NO: 5 (Vc-n-01-ST(H)) | LIDCCEI CCNPACF GCLN |
| SEQ ID NO: 6 (Y-STa) | QACDPPSPPAEVSSDWDCCDV CCNPACA GC |
| SEQ ID NO: 7 (Y-STb) | KACDTQTPSPSEENDDWCCEV CCNPACA GC |
| SEQ ID NO: 8 (Y-STc) | AECTQSATTQGENDWDWCCEL CCNPACF GC |

(J. Peptide Res., 63, 2004/200-206. (The table above compares amino acid sequences of heat-stable entero-toxins elaborated by various enteric bacteria. The numbers of amino acid residues are referred to Ec-STp. Invariant residues are indicated by hatched letters. In specific embodiments, a variant or mutant enterotoxin comprises one or more mutations of amino acids that are not at the positions of the invariant residues or alternatively comprises one or more conservative mutations of amino acids that are at the positions of the invariant residues as shown.)

In an exemplary embodiment, STa is used as the diarrhea-inducing agent. STa is a potent toxin which—depending at least in part on its level of purity and/or biological activity—can induce diarrhea in humans if ingested in quantities as low as about 5 micrograms (mcg) or lower.

Examples of STa amino acid sequences are as follows:

```
ASN-THR-PHE-TYR-CYS-CYS-GLU-LEU-CYS-    SEQ ID NO: 9
CYS-ASN-PRO-ALA-CYS-ALA-GLY-CYS-TYR
```

-continued

```
ASN-SER-SER-ASN-TYR-CYS-CYS-GLU-LEU-    SEQ ID NO: 10
CYS-CYS-ASN-PRO-ALA-CYS-THR-GLY-CYS-
TYR
```

According to Thompson and Giannella, Infection and Immunity (1985) 47:834-836, all heat-stable enterotoxins composed of 18 amino acids sequenced then from human, porcine, and bovine isolates of *E. coli* have identical primary structures, i.e., (SEQ ID NO: 9) ASN-THR-PHE-TYR-CYS-CYS-GLU-LEU-CYS-CYS-ASN-PRO-ALA-CYS-ALA-GLY-CYS-TYR. Furthermore, all 18- and 19-amino-acid heat-stable enterotoxins from *E. coli* share an almost identical core sequence, i.e., 14 of the 15 carboxy-terminal amino acid residues are identical.

As used herein, "sequence identity" (or "% identical") means the percentage of identical amino acid residues at corresponding positions in two or more sequences when the sequences are aligned to maximize sequence matching, i.e., taking into account gaps and insertions. Identity can be readily calculated by known methods, including but not limited to those described in Computational Molecular Biology, Lesk, A. M., ed., Oxford University Press, New York, 1988, Biocomputing: Informatics and Genome Projects, Smith, D. W., ed., Academic Press, New York, 1993, Computer Analysis of Sequence Data, Part I, Griffin, A. M., and Griffin, H. G., eds., Humana Press, New Jersey, 1994, Sequence Analysis in Molecular Biology, von Heinje, G., Academic Press, 1987, and Sequence Analysis Primer, Gribskov, M. and Devereux, J., eds., M Stockton Press, New York, 1991, and Carillo, H., and Lipman, D., SIAM J. Applied Math., 48: 1073 (1988). Methods to determine identity are designed to give the largest match between the sequences tested. Moreover, methods to determine identity are codified in publicly available computer programs. Computer program methods to determine identity between two sequences include, but are not limited to, the GCG program package (Devereux, J., et al., Nucleic Acids Research 12(1): 387 (1984)), BLASTP, BLASTN, and FASTA (Altschul, S. F. et al., J. Molec. Biol. 215: 403-410 (1990) and Altschul et al. Nuc. Acids Res. 25: 3389-3402 (1997)). The BLAST X program is publicly available from NCBI and other sources (BLAST Manual, Altschul, S., et al., NCBI NLM NIH Bethesda, Md. 20894, Altschul, S., et al., J. Mol. Biol. 215: 403-410 (1990). The well known Smith-Waterman algorithm may also be used to determine sequence identity.

The phrase "conservative amino acid substitution" refers to grouping of amino acids on the basis of certain common properties. A functional way to define common properties between individual amino acids is to analyze the normalized frequencies of amino acid changes between corresponding proteins of homologous organisms (Schulz, G. E. and R. H. Schirmer., Principles of Protein Structure, Springer-Verlag). According to such analyses, groups of amino acids may be defined where amino acids within a group exchange preferentially with each other, and therefore resemble each other most in their impact on the overall protein structure (Schulz, G. E. and R. H. Schirmer, Principles of Protein Structure, Springer-Verlag). Examples of amino acid groups defined in this manner include:

(i) a charged group, consisting of Glu and Asp, Lys, Arg and His, (ii) a positively-charged group, consisting of Lys, Arg and His, (iii) a negatively-charged group, consisting of Glu and Asp, (iv) an aromatic group, consisting of Phe, Tyr and Trp, (v) a nitrogen ring group, consisting of His and Trp, (vi) a large aliphatic nonpolar group, consisting of Val, Leu and Ile, (vii) a slightly-polar group, consisting of Met and Cys, (viii) a small-residue group, consisting of Ser, Thr, Asp, Asn, Gly, Ala, Glu, Gln and Pro, (ix) an aliphatic group consisting of Val, Leu, Ile, Met and Cys, and (x) a small hydroxyl group consisting of Ser and Thr.

In addition to the groups presented above, each amino acid residue may form its own group, and the group formed by an individual amino acid may be referred to simply by the one and/or three letter abbreviation for that amino acid commonly used in the art.

"Peptidomimetic" as used herein refers to a compound in which at least a portion of a subject peptide of the application (e.g., an enterotoxin peptide) is modified, and the three dimensional structure of the peptidomimetic remains substantially the same as that of the polypeptide. Peptidomimetics may be analogues of a subject polypeptide of the application (e.g., an enterotoxin) that are, themselves, polypeptides containing one or more substitutions or other modifications within the subject polypeptide sequence. Alternatively, at least a portion of the subject polypeptide sequence may be replaced with a nonpeptide structure, such that the three-dimensional structure of the subject polypeptide is substantially retained. In addition, other peptide portions of the subject peptide may, but need not, be replaced with a non-peptide structure. Peptidomimetics (both peptide and non-peptidyl analogues) may have improved properties (e.g., decreased proteolysis, increased retention or increased bioavailability). Peptidomimetics may have improved oral availability. Each peptidomimetic may further have one or more unique additional binding elements.

The amount of STa in each pill for human consumption, therefore, should be below about 5 mcg, and even lower if the several pills are to be permitted before diarrhea is induced. Typically, the amount of the diarrheagenic substance is a function of one or more factors, such as type and features of the specimen, desired rapidity of diarrhea onset, toxicity of the diarrheagenic substance, etc. Exemplary ranges for STa dosage are given in a subsequent section below.

In the small intestine, a coating of STa dissolves and binds to STa receptors in the GI tract. Typically, STa induces a rapid-onset, significant, and usually involuntary diarrhea in the GI tract. Rapid-onset diarrhea refers herein to a diarrhea that is induced in approximately 15-30 minutes after ingestion.

In various other practices, the compositions, compositions, and methods described herein employ other diarrhea-inducing materials such as a diarrhoetic chemical (as alternatives to, or in conjunction with, the diarrheagenic substances described above). Selection of such a diarrheagenic chemical is guided at least in part by one or more of the following desirable, and in some instances essential, properties: a fast-clearance property to reduce or substantially prevent a build-up of the chemical in the body of the specimen over time; reduced, acceptable, minimal, or in some instances even negligible long-term side effects and toxicities (other than the diarrheagenic properties); and suitability for producing a rapid-onset, severe diarrhea (to prevent, or substantially reduce, absorption of the therapeutic compound in the GI tract when taken in excess of approximately the recommended or threshold dose).

In a typical embodiment, the diarrheagenic coating includes a biological agent, a chemical substance, or a biochemical compound having purgative or cathartic properties that promote rapid peristalsis in the GI tract. Examples of a chemical substance having one or more of such properties include, for example and without limitation, acetylcholine, and acetylcholine esterase inhibitors (neostigmine).

Exemplary Enteric Substances

Enteric substances as employed by the compositions and methods described herein- and described above in relation to the figures (e.g., layer 103 of FIG. 1A)—include, for example and without limitation, one or more suitable hydrophilic polymers such as, without limitation, hydroxypropylmethyl cellulose; carbomers; polyethylene oxides; hydroxypropyl cellulose; hydroxyethyl cellulose; carboxymethylcellulose; sodium carboxymethylcellulose; carboxyvinylpolymers; polyvinyl alcohols; glucans; scleroglucans; mannans; xanthans; carboxymethylcellulose and its derivatives; methylcellulose; cellulose; crosslinked polyvinylpyrrolidone; carboxymethyl starch; potassium methacrylatedivinylbenzene copolymer; hydroxypropylcyclodextrin; alpha, beta, gamma cyclodextrin or derivatives and other dextran derivatives; natural gums; seaweed extract; plant exudate; agar; agarose; algin; sodium alginate; potassium alginate; carrageenan; kappa-carrageenan; lambda-carrageenan; fucoidan, furcellaran; laminarin; hypnea; eucheuma; gum arabic; gum ghatti; gum karaya; gum tragacanth; guar gum; locust bean gum; quince psyllium; flax seed; okra gum; arabinogalactin; pectin; scleroglucan; dextran; amylose; amylopectin; dextrin; acacia; karaya; guar; a swellable mixture of agar and carboxymethyl cellulose; a swellable composition comprising methyl cellulose mixed with a sparingly crosslinked agar; a blend of sodium alginate; and locust bean gum.

Additionally, or alternatively, the enteric coating may include one or more enteric polymer materials such as, without limitation, cellulose acetate phthalate, cellulose acetate trimaletate, hydroxypropyl methylcellulose phthalate, polyvinyl acetate phthalate, EUDRAGIT® poly acrylic acid and polyacrylate and methacrylate coatings, polyvinyl acetaldiethylamino acetate, hydroxypropyl methylcellulose acetate succinate, cellulose acetate trimellitate, shellac; hydrogels and gel-forming materials, such as carboxyvinyl polymers, sodium alginate, sodium carmellose, calcium carmellose, sodium carboxymethyl starch, polyvinyl alcohol, hydroxyethyl cellulose, methyl cellulose, gelatin, starch and cellulose-based cross-linked polymers.

Additionally, or alternatively, the enteric coating may include one or more suitable pH modifiers. Examples of suitable pH modifiers include, without limitation, one or more of: an organic acid such as citric acid, fumaric acid, tartaric acid, succinic acid, ascorbic acid, acetic acid, malic acid, glutaric acid and adipic acid; a salt of these or of inorganic acids; and magnesium hydroxide, etc.

Target Population

The compositions and methods described herein can be used to formulate therapeutic or other pharmacological compositions in humans or other animals. The subject can be a human or animal patient in a general population or in a particular population. For example, a subject can be a pediatric patient, a pregnant or nursing woman, an elderly patient, or a patient having another condition or disease (e.g., an addiction to the pharmaceutically active agent or a hepatic disease) that makes the patient more vulnerable to a higher-than-desirable level of the specific pharmaceutically active agent or any pharmaceutically active agent. Applicant considers the scope of the application to also include non-therapeutic or non-pharmacological compositions; for example, certain compositions intended for non-human consumption can be formulated by employing the compositions and methods described herein to prevent accidental ingestion by children. Moreover, the compositions and methods described herein can be used to regulate administration of medical, chemical, and/or biological substances or agents to not only humans, but also animal target populations.

Dosage Control

According to one illustrative practice, a diarrhoetic dose level per pill is determined using a constraint-based algorithm as follows:

Number of pills ingested to reach serious toxic or lethal dose×Diarrhoetic dose per pill=Total amount of diarrhoetic needed to elicit rapid diarrheal reflex.

Diarrhoetic dose per pill×Number of pills needed for appropriate therapeutic dose=Total amount of diarrhoetic that a target specimen (e.g., human) can tolerate before diarrhea is induced.

Solve the equations above for the value of diarrhoetic dose per pill.

According to one practice, the diarrhoetic dose level per pill is determined at least in part to induce diarrhea if one or more pills are consumed by a specimen other than an intended specimen. For example and without limitation, a young child (e.g., below about 5 years of age) typically has an increased diarrheal response to STa in comparison with an adult (e.g., a human specimen approximately at or above 18 years of age) such that a specific amount of STa in a pill may be insufficient to elicit a diarrheal response in the adult, but sufficient to elicit a fast, and in some instances severe, diarrheal response in the child.

Exemplary Ranges of STa in Various Embodiments

In various embodiments, the amount of STa included in each pill conforms to one, or a union of more than one, of the following ranges: less than about 250 nanograms (ng); less than about 500 ng; between about 250 ng and about 500 ng; less than about 750 ng; between about 500 ng and about 750 ng; less than about 1000 ng (i.e., 1 mcg); between about 750 ng and about 1 mcg; less than about 2 mcg; between about 1 mcg and about 2 mcg; less than about 3 mcg; between about 2 mcg and about 3 mcg; less than about 4 mcg; between about 3 mcg and about 4 mcg; less than about 5 mcg; between about 4 mcg and about 5 mcg; less than about 6 mcg; between about 5 mcg and about 6 mcg; less than about 7 mcg; between about 6 mcg and about 7 mcg; less than about 8 mcg; between about 7 mcg and about 8 mcg; less than about 9 mcg; between about 8 mcg and about 9 mcg; less than about 10 mcg; between about 9 mcg and about 10 mcg; less than about 20 mcg; between about 10 mcg and about 20 mcg; less than about 30 mcg; between about 20 mcg and about 30 mcg; less than about 40 mcg; between about 30 mcg and about 40 mcg; less than about 50 mcg; between about 40 mcg and about 50 mcg; less than about 60 mcg; between about 50 mcg and about 60 mcg; less than about 70 mcg; between about 60 mcg and about 70 mcg; less than about 80 mcg; between about 70 mcg and about 80 mcg; less than about 90 mcg; between about 80 mcg and about 90 mcg; less than about 100 mcg; between about 90 mcg and about 100 mcg; less than about 150 mcg; between about 100 mcg and about 150 mcg; less than about 200 mcg; between about 150 mcg and about 200 mcg; less than about 250 mcg; between about 200 mcg and about 250 mcg; less than about 300 mcg; between about 250 mcg and about 300 mcg; less than about 350 mcg; between about 300 mcg and about 350 mcg; less than about 400 meg; between about 350 mcg and about 400 mcg; less than about 450 mcg; between about 400 mcg and about 450 mcg; less than about 500 mcg; between about 450 mcg and about 500 mcg; less than about 550 mcg; between about 500 mcg and about 550 mcg; less than about 600 mcg; between about 550 mcg and about 600 mcg; less than about 650 mcg; between about 600 mcg and about 650 mcg; less than about 700 mcg; between about 650 mcg and about 700 mcg; less than about 750 meg; between about 700 mcg and about 750 meg; less than about 800 mcg; between about 750 mcg and about 800 mcg; less than about 850 mcg; between about 800 mcg and about 850 mcg; less than about 900 mcg; between about 850 mcg and about 900 mcg; less than about 950 mcg; between about 900 mcg and about 950 mcg; less than about 1 milligram (mg); between about 950 mcg and about 1 mg; less than about 5 mg; between about 1 mg and about 5 mg; less than about 10 mg; between about 5 mg and about 10 mg; less than about 15 mg; between about 10 mg and about 15 mg; less than about 20 mg; between about 15 mg and about 20 mg; less than about 50 mg; between about 20 mg and about 50 mg; less than about 100 mg; and between about 50 mg and about 100 mg.

Additional support for the illustrative methods, compositions, and compositions of the present application are described in, for example, U.S. Pat. No. 6,897,205, Multiparticulate form of medicament and U.S. Pat. No. 6,902,742, Multiparticulate modified release composition.

The '205 patent describes a multiparticulate drug form suitable for uniform release of an active pharmaceutical ingredient in the small intestine and in the large intestine, comprising at least two forms of pellets A and B which comprise an active pharmaceutical ingredient in the core and have different polymer coatings which determine the release of the active ingredient at different pH values, characterized in that pellet form A is provided with an inner polymer coating which enables continuous release of active ingredient, and has an outer enteric coating which rapidly dissolves above about pH 5.5, and pellet form B is provided with an inner polymer coating which, in the USP release test, releases less than 20% of the active ingredient at pH 6.8 in 6 hours and releases more than 50% of the active ingredient at pH 7.2 in 6 hours. The '205 patent further describes a process for producing a multiparticulate drug form by the different pellet forms A and B being produced by coating active ingredient-containing cores with the stated polymer coatings, being mixed together and being converted into a multiparticulate drug form by introduction into a capsule or compression to a tablet unit in the presence of excipients. The '205 patent also describes the use of the described pellet forms A and B in the claimed process for producing a multiparticulate drug form with uniform release of active ingredient in the pH range of 6.8 and 7.2, corresponding to the conditions in the small and large intestine, in particular for the treatment of Crohn's disease or ulcerative colitis.

The '742 patent discloses a multiparticulate modified release composition having a first component comprising a first population of active ingredient-containing particles and a second component comprising a second population of active ingredient-containing particles. The active ingredient contained in the first and second components can be the same or different and active ingredient-containing particles of the second component are coated with a modified release coating. Alternatively or additionally, the second population of active ingredient containing particles further comprises a modified release matrix material. Following oral delivery, the composition in operation delivers the active ingredient or active ingredients in a pulsatile manner. The '742 patent further provides a multiparticulate modified release composition of which the first component is an immediate release (IR) component. Further, the modified release coating applied to the second population of active ingredient containing particles causes a lag time between the release of active ingredient from the first population of active ingredient containing particles and the release of active ingredient from the second population of active ingredient containing particles. Similarly, the presence of a modified release matrix material in the second population of active ingredient containing particles causes a lag time between the release of active ingredient from the first population of active ingredient containing particles and the release of active ingredient from the second population of active ingredient containing particles. The duration of the lag time may be varied by altering the composition and/or the amount of the modified release coating and/or altering the composition and/or amount of modified release matrix material utilized. Thus, the duration of the lag time can be designed to mimic a desired plasma profile. Because the plasma profile produced by the multiparticulate modified release composition upon administration is substantially similar to the plasma profile produced by the administration of two or more IR dosage forms given sequentially, the multiparticulate controlled release composition described in the '742 patent is particularly useful for administering active ingredients for which patient tolerance may be problematical. This multiparticulate modified release composition is therefore advantageous for reducing or minimizing the development of patient tolerance to the active ingredient in the composition.

EXAMPLES

The Examples described below involve animal models. Although Applicant has included and will continue to include adult mice as study subjects, other animal models are also contemplated. For example, models based on cats, dogs, pigs, piglets, calves, rabbit, rats, and primates can also be employed for the testing described below. Animal maintenance and treatments were and will be conducted in accordance with the National Institute of Health Guide for Animal Welfare, as approved by Institutional Animal Care and Use Committee. Further, toxicity, safety, and efficacy studies will be conducted through human clinical trials in cases where the compositions of the application are intended for human use. Such clinical trials will be designed and conducted using protocols approved under applicable laws and regulations.

Example 1

Establishment of STa Dose-Response Curve of STa to Establish Diarrheagenic Dose in a Population of Adult Mice Diarrheal Response Assay 0.5 ml of 10% glucose solution with STa at different dilutions were administered to adult male Swiss Webster mice (each weighing 27-33 grams) by gavage. Mice were weighed prior to STa challenge. At each dilution of STa, 10 mice were utilized for establishing a statistical characterization of the diarrheal response (mean and standard deviation). After STa challenge, at approximately 90 minutes, the animals were sacrificed and the gut is removed and weighed. The remaining carcass is also weighed. The gut/body weight ratio is established as the in-vivo assay of quantifying the diarrheal response to exogenous STa.

Results are shown below:

| Mouse Group (10 Mice in each Group) | Mean (Gut/Body Weight) Ratio | Standard Deviation |
|---|---|---|
| Control (Saline) | .1084 | .0066 |
| 10 MU of STa | .1066 | .0094 |
| 100 MU of STa | .1144 | .0065 |
| 1000 MU of STa | .1339 | .0047 |

***One MU is the amount of toxin which produces an intestinal weight/carcass weight ratio of ≧0.083 in 3-day-old mice.

Giannella describes a suckling mouse model for detection of a heat-stable *E. coli* enterotoxin, Infection and Immunity (1976) 14:95-99.

Characterization of the Diarrheal Dose Response Curve

In a pharmaceutical composition including the STa peptide with a therapeutically active compound, the amount of STa peptide released from a pill, tablet, capsule, or any oral pharmaceutical composition should not elicit a diarrheal response in a human or animal if the dose of the pharmaceutical composition is approximately equal to the recommended therapeutic dose of the composition. However, the cumulative amount of STa peptide should be enough to elicit a diarrheal response in a human or animal if the pharmaceutical composition is administered in amounts significantly exceeding the therapeutic dose and approaching quantities that would be toxic, or lethal, or otherwise harmful to a human or animal.

Example 2

Dose-Response Curve for Acetaminophen-Induced Hepatotoxicity

Data from several studies suggests that acetaminophen is responsible for 39 percent of all cases of acute liver failure in the United States. E.g., Lee, New England J. Med. (2003) 349: 474-485, Shankar et al., Toxicol. Sci. (2003) 73: 220-234. Acetaminophen-induced hepatotoxicity is also a well-established model of fulminant hepatic failure. E.g., Newsome et al., Liver Transplantation (2000) 6: 21-31.

Acetaminophen Administration

Food, but not water, will be removed 12 hours before acetaminophen administration. The method for acetaminophen administration will be as described by Walker et al, Lab Invest. (1980) 42:181-189. Briefly, acetaminophen will be dissolved in warm distilled water at various dilutions and given to mice by gavage at a volume of 0.5 ml. At each dilution of acetaminophen, 5 mice will be utilized for statistical characterization (mean and standard deviation) of physiologic responses to acetaminophen challenges.

Dilutions of Acetaminophen to be administered (mg/kg):

| | | | | | | | | | |
|---|---|---|---|---|---|---|---|---|---|
| 0 | 5 | 20 | 40 | 80 | 100 | 200 | 500 | 750 | 1000 |

At 6 hours post acetaminophen challenge, blood samples for biochemical assays will be collected under diethyl ether anesthesia.

Histopathology

At 6 hours post acetaminophen challenge (and after blood samples have been collected), livers will be surgically removed from mice under diethyl ether anesthesia. Portions of liver will be taken from the left lateral lobes and washed with ice-cold normal saline (0.9% NaCl), cut into small pieces, and fixed immediately in 10% phosphate-buffered formalin for 48 h. The liver tissue will then be transferred to 70% ethyl alcohol and stored until processed. The liver specimens will be processed, embedded in paraffin, sectioned at 5 μm, and stained with hematoxylin and eosin (H&E) for histological examination under a light microscope. The extent of liver injury will be estimated by certified pathologists from the animal disease diagnostic laboratory of Michigan State University.

Biochemistry Assays

From the collected blood samples, plasma alanine aminotransferase (ALT) will be determined as a biochemical marker of liver damage. The plasma acetaminophen levels will also be determined using standard assays (Walker et al., supra).

Example 3

Evaluation of Protective Drug Delivery Model to Prevent Acetaminophen-Induced Hepatic Failure in Adult Mice In this section, a formulation of acetaminophen combined with STa will be evaluated for preventing hepatotoxicity due to acute acetaminophen overdosing. There will be three experimental groups and one control group. Group A will include mice administered a hepatotoxic dose of acetaminophen in a particulate (solid) form after a diarrheagenic dose of STa. Group B will include mice administered a hepatotoxic dose of acetaminophen dissolved in solution after a diarrheagenic dose of STa. Group C will include mice administered a therapeutic dose of acetaminophen in particulate (solid) form after a non-diarrheagenic dose of STa. The control group will consist of mice administered a hepatotoxic dose of acetaminophen in particulate (solid) form without any STa administration. Each experimental group and the control group will consist of 5 mice. Mice will be weighed at the beginning of the experiment and six hours after acetaminophen challenge. During this interval, mice will not be afforded water or solid nutrition.

Administration of STa to Experiment Groups

As determined in section 1, a diarrheagenic dose of STa will be administered by gavage to mice from groups A and B 30 minutes prior to acetaminophen challenge. Group C mice will be administered a non-diarrheagenic dose of STa (approximately 5% of the dose of a diarrheagenic response as determined in section 1). The control mice will not be administered any STa (only 0.5 ml of 10% glucose) 30 minutes prior to acetaminophen challenge.

Acetaminophen Administration 30 minutes after STa administration, mice from group A will be administered a hepatotoxic dose of acetaminophen prepared in solid formulation (15-20 mg), by gavage.

Thirty minutes after ST administration, mice from group B will be administered a hepatotoxic dose of acetaminophen in 0.5 ml bolus solution. The acetaminophen solution will be prepared by dissolving acetaminophen in warm distilled water. The concentration will be determined from the results of section 2.

In the group C mice, a therapeutic dose of acetaminophen (approximately 10 mg/kg) will be administered using a 0.5 ml bolus solution 30 minutes after a non-diarrheagenic STa challenge. Approximately 90 minutes after acetaminophen administration, blood samples will be drawn under diethyl ether anesthesia. Then, mice will be sacrificed under diethyl ether anesthesia and liver tissue samples will be obtained as described in the preceding section.

Control mice will be given a solid formulation of acetaminophen at a hepatotoxic dose. Control mice will not be administered any STa prior to the acetaminophen challenge.

Biochemical Assays and Histopathology

In the experimental groups A and B, and the control group, the mice will be sacrificed 6 hours after acetaminophen challenge under diethyl ether anesthesia. Prior to sacrifice, blood samples will be drawn under anesthesia to measure ALT and acetaminophen levels in plasma. Liver samples will be obtained and processed and submitted for histopathology.

Results and Analysis of Data

The plasma ALT levels in experimental groups A, B, C, and the control groups will be compared to determine whether the STa treatment along with the toxic levels of acetaminophen resulted in a significant reduction of the hepatotoxicity as measured by normal or near normal serum ALT levels. Histopathology to visually identify necrosis and evidence of acute liver injury will be a second means of assessing acetaminophen effects with and without prior STa administration. The difference in mice weights at the beginning and end of the experiments (6 hour duration) will be considered as a surrogate for the magnitude of the secretory diarrheal response. The acetaminophen plasma levels will also be measured in all groups to investigate whether STa-induced secretory diarrhea significantly reduces the bioavailability of acetaminophen.

INCORPORATION BY REFERENCE

All references including scientific literature and patent literature cited herein are hereby incorporated by reference in their entirety.

EQUIVALENTS

Many other equivalents to the specific embodiments of the application and the specific aspects and practices associated with the compositions and methods described herein exist. Accordingly, the application is not to be limited to the embodiments, aspects, practices, and methods disclosed herein, but it is to be understood from the following claims, which are to be interpreted as broadly as allowed under the law.

I claim:

1. A therapeutic composition comprising:

a pharmaceutically active agent; and a diarrheagenic agent that is an enterotoxin comprising an amino acid sequence that is 95% identical to SEQ ID NO: 9; and wherein said diarrheagenic agent induces diarrhea to reduce the harmful or undesired side effects of the pharmaceutically active agent when the pharmaceutically active agent is ingested at a dose higher than the prescribed dose.

2. The therapeutic composition of claim 1, wherein the therapeutic composition is formulated such that ingestion by a subject of the therapeutic composition at or lower than the prescribed dosage does not cause diarrhea in the subject.

3. The therapeutic composition of claim 1, wherein the diarrheagenic agent is coated onto the pharmaceutically active agent.

4. The therapeutic composition of claim 1, further comprising an additional coating.

5. The therapeutic composition of claim 4, wherein the additional coating comprises an enteric coating.

6. The therapeutic composition of claim 1, wherein the therapeutic composition comprises an orally administrable dosage form.

7. The therapeutic composition of claim 6, wherein orally administrable dosage form is a tablet.

8. A therapeutic composition comprising:

a pharmaceutically active agent; and a diarrheagenic agent;

wherein the diarrheagenic agent is an enterotoxin comprising an amino acid sequence at least 95% identical to SEQ ID NO: 9; and said therapeutic composition comprises less than about 1 mg of the enterotoxin.

9. A method for reducing harmful or undesired side effects in a subject, caused by ingestion of a pharmaceutically active agent at a dose higher than the prescribed dosage comprising:

administering to the subject a therapeutic composition comprising:

a) a pharmaceutically active agent; and b) a diarrheagenic agent comprising an amino acid sequence at least 95% identical to SEQ ID NO: 9;

wherein said diarrheagenic agent induces diarrhea to reduce the harmful or undesired side effects of the pharmaceutically active agent when the pharmaceutically active agent is ingested at a dose higher than the prescribed dose.

10. The therapeutic composition of claim 1 or 8, wherein the pharmaceutically active agent is selected from antidiabetic, analgesic, antiinflammatory agent, antirheumatic, antihypotensive agent, anti hypertensive agent, psychoactive drug, tranquilizer, antiemetic, muscle relaxant, glucocorticoid, agent for treating an inflammatory bowel disease, antiallergic, antibiotic, antiepileptic, anticoagulant, antimycotic, antitussive, arteriosclerosis remedy, diuretic, protein, peptide, enzyme, enzyme inhibitor, gout remedy, hormone, hormone inhibitor, cardiac glycoside, immunotherapeutic agent, cytokine, laxative, lipid-lowering agent, migraine remedy, mineral product, otological agent, anti-Parkinson agent, thyroid therapeutic agent, spasmolytic, platelet aggregation inhibitor, vitamin, cytostatic inhibitor, metastasis inhibitor, phytopharmaceutical, chemotherapeutic agent, amino acid(s), and any combination thereof.

11. The method of claim 9, wherein the pharmaceutically active agent is selected from antidiabetic, analgesic, antiinflammatory agent, antirheumatic, antihypotensive agent, anti hypertensive agent, psychoactive drug, tranquilizer, antiemetic, muscle relaxant, glucocorticoid, agent for treating an inflammatory bowel disease, antiallergic, antibiotic, antiepileptic, anticoagulant, antimycotic, antitussive, arteriosclerosis remedy, diuretic, protein, peptide, enzyme, enzyme inhibitor, gout remedy, hormone, hormone inhibitor, cardiac glycoside, immunotherapeutic agent, cytokine, laxative, lipid-lowering agent, migraine remedy, mineral product, otological agent, anti-Parkinson agent, thyroid therapeutic agent, spasmolytic, platelet aggregation inhibitor, vitamin, cytostatic inhibitor, metastasis inhibitor, phytopharmaceutical, chemotherapeutic agent, amino acid(s), and any combination thereof.

* * * * *